(12) United States Patent
Murata et al.

(10) Patent No.: US 7,297,815 B2
(45) Date of Patent: Nov. 20, 2007

(54) PROCESS FOR PRODUCING FLUORINATED SULFONYL FLUORIDE COMPOUND

(75) Inventors: Koichi Murata, Yokohama (JP); Takashi Okazoe, Yokohama (JP); Eisuke Murotani, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 11/322,396

(22) Filed: Jan. 3, 2006

(65) Prior Publication Data

US 2006/0106252 A1 May 18, 2006

Related U.S. Application Data

(63) Continuation of application No. PCT/JP2004/009779, filed on Jul. 2, 2004.

(30) Foreign Application Priority Data

Jul. 2, 2003 (JP) ............................. 2003-270412

(51) Int. Cl.
C07C 309/00 (2006.01)
(52) U.S. Cl. .......................................... 562/825; 562/1
(58) Field of Classification Search ................ 562/825, 562/1
See application file for complete search history.

(56) References Cited

U.S. PATENT DOCUMENTS

| | | | |
|---|---|---|---|
| 2,743,290 | A | 4/1956 | Stewart |
| 4,940,814 | A | 7/1990 | Schwertfeger |
| 5,093,432 | A | 3/1992 | Bierschenk et al. |
| 5,466,877 | A | 11/1995 | Moore |
| 6,790,982 | B2 | 9/2004 | Ito et al. |
| 2004/0181091 | A1 | 9/2004 | Ito et al. |

FOREIGN PATENT DOCUMENTS

| | | |
|---|---|---|
| DE | 37 07 367 | 9/1988 |
| EP | 0 314 380 | 5/1989 |
| GB | 2118541 | 11/1983 |
| JP | 56-90054 | 7/1981 |
| WO | 02/44138 | 6/2002 |
| WO | 03/106515 | 12/2003 |
| WO | 2004/094365 | 11/2004 |

OTHER PUBLICATIONS

Forohar et al. Synthesis and reactions of the b-sultone of perfluorovinylsulfonyl Fluoride, Journal of Fluorine Chemistry, 66 (1994) 101-104.*
U.S. Appl. No. 11/318,978, filed Dec. 28, 2005, Murata et al.
U.S. Appl. No. 11/322,396, filed Jan. 3, 2006, Murata et al.
Methods of Organic Chemistry (Houben-Weyl), 4th Ed., Baasner, B., Hagemann H., Tatlow, J.C., Eds, Georg Thieme, Stuttgart, vol. E 10b, (Organo-Fluorine Compounds) Part 1, pp. 703-704 (1999).
Forochar, F., Et al., Journal of Fluorine Chemistry, vol. 66, pp. 101-104 (1994).
Scott R.B., Jr., et al., The Journal of Organic Chemistry, vol. 21, No. 4, pp. 385-387 (1956).
Gramstad, T., et al., J. Chem. Soc., Perfluroalkyl Derivatives of Sulphur, Part IV, Perfluoroalkanesulphonic Acids, pp. 173-180 (1956).
Mohtasham, et al., Journal of Fluorine Chemistry, vol. 42, No. 1, pp. 119-136 (1989).

* cited by examiner

Primary Examiner—Yvonne (Bonnie) Eyler
Assistant Examiner—Chukwuma Nwaonicha
(74) Attorney, Agent, or Firm—Oblon, Spivak, McClelland, Maier & Neustadt, P.C.

(57) ABSTRACT

It is an object of the present invention to solve difficulty in production and to provide a process to obtain fluorinated sulfonyl fluoride compound having various molecular structures efficiently at a low cost.

That is, the present invention provides a process which comprises reacting $(FSO_2—)_n R^A(-E-R^B)_m$ (1F) with fluorine in a liquid phase to form $(FSO_2—)_n R^{AF}(-E^F-R^{BF})_m$ (2), and decomposing this compound to obtain $(FSO_2—)_n R^{AF}(-E^{F1})_m$ (3), provided that $R^A$ is a (n+m) valent organic group having at least two carbon atoms, $R^{AF}$ is a group having $R^A$ fluorinated, or the like, each of $R^B$ and $R^{BF}$ is a fluorinated monovalent organic group, or the like, E is —COOCH$_2$— or the like, $E^F$ is —COOCF$_2$— or the like, $E^{F1}$ is —COF or the like, n is an integer of at least 2, and m is an integer of at least 1.

15 Claims, No Drawings

PROCESS FOR PRODUCING FLUORINATED SULFONYL FLUORIDE COMPOUND

TECHNICAL FIELD

The present invention relates to a process for producing fluorinated sulfonyl fluoride compounds useful as e.g. materials for ion-exchange resins, and novel compounds useful as intermediates in the process.

BACKGROUND ART

Fluorinated sulfonyl fluoride compounds are compounds useful as materials for ion-exchange resins. As a process for producing such compounds, the following processes have been known.

(1) A process of reacting a cyclic compound obtained by a reaction of tetrafluoroethylene with sulfur trioxide ($SO_3$) with a perfluoroalkylene oxide such as hexafluoropropylene oxide (for example, a process represented by the following scheme and WO02/44138):

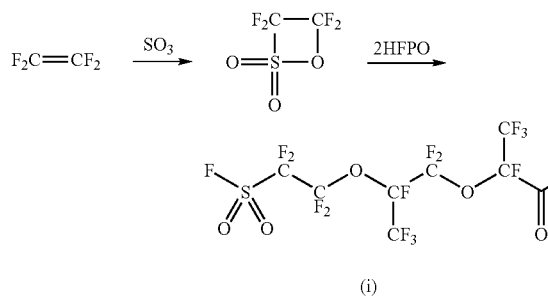

(i)

(2) A process of converting a hydrocarbon sulfonic acid derivative having a hydroxyl group as a starting material into an ester with a fluorinated carboxylic acid, which is directly fluorinated and then pyrolized (WO02/44138).

(3) A process for producing a compound having two fluorosulfonyl groups and one fluoroformyl group in 5 combination by a process described by the following scheme (F. Forohar, D. D. DesMarteau, Journal of Fluorine Chem., 1994, 66, 101):

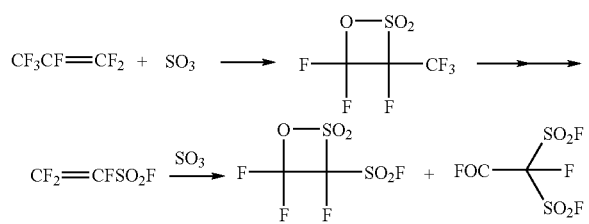

However, the process (1) is a disadvantageous process for practical industrial application, since due care is required for handling $SO_3$. Further, this process is economically disadvantageous because the difficulty in synthesis is high. In addition, the product is limited to a compound having a side chain (such as a —$CF_3$), whereby there is a problem from the viewpoint of the performance and the membrane characteristics of an ion-exchange membrane to be formed.

The process (2) is a process to solve the drawback of the process (1), but availability of the compound having a fluorosulfonyl group as a starting material is limited, whereby the compound to be produced is limited in some cases. Further, the product is a compound having only one fluorosulfonyl group.

The process (3) is disadvantageous as an industrial production process, since $SO_3$ is employed in two steps. Further, the skeleton of the compound is limited.

DISCLOSURE OF THE INVENTION

The present invention has been made to solve the problems of the conventional processes, and it is an object of the present invention to provide a process for producing fluorinated sulfonyl fluoride compounds having various molecular structures and having an optional number of fluorosulfonyl groups from easily available materials.

The present invention provides:

(1) A process for producing a fluorinated sulfonyl fluoride compound represented by the following formula (3), which comprises reacting a compound represented by the following formula (1F) with fluorine in a liquid phase to obtain a compound represented by the following formula (2), and then decomposing the compound represented by the formula (2) to obtain a compound represented by the following formula (3):

$$(FSO_2-)_n R^A(-E-R^B)_m \qquad (1F)$$

$$(FSO_2-)_n R^{AF}(-E^F-R^{BF})_m \qquad (2)$$

$$(FSO_2-)_n R^{AF}(-E^{F1})_m \qquad (3)$$

wherein $R^A$ is a (n+m)valent organic group having at least two carbon atoms;

$R^B$ is a monovalent organic group;

E is a bivalent connecting group;

$R^{AF}$ is the same group as $R^A$ or a (n+m)valent organic group having $R^A$ fluorinated;

$R^{BF}$ is the same group as $R^B$ or a monovalent organic group having $R^B$ fluorinated;

$E^F$ is the same group as E or a bivalent connecting group having E fluorinated;

$E^{F1}$ is a monovalent group formed by decomposition of $E^F$;

n is an integer of 2 or more; and m is an integer of 1 or more;

provided that at least one of $R^A$, $R^B$ and E is a group capable of being fluorinated, and at least one of $R^{AF}$, $R^{BF}$ and $E^F$ is a group formed by fluorination of $R^A$, $R^B$ or E, respectively.

(2) The process according to (1), wherein a compound represented by the following formula (7) is oxidized by means of an oxidizing agent essentially containing a halogen atom to obtain a compound represented by the following formula (1), and in a case that X in the compound represented by the formula (1) is a fluorine atom, such a compound is used as the compound represented by the formula (1F), and in a case that X in the compound represented by the formula (1) is a halogen atom other than a fluorine atom, such X is converted into a fluorine atom, and the obtained compound is used as the compound represented by the formula (1F), provided that in the following formulae, $R^A$, E, $R^B$, n and m are as defined above, Y is a hydrogen atom, a monovalent organic group or a —$SO_3^-M^+$ group (wherein M is an alkali metal atom), and X is a halogen atom:

$$(Y-S-)_n R^A(-E-R^B)_m \qquad (7)$$

$$(XSO_2-)_n R^A(-E-R^B)_m \qquad (1)$$

(3) The process according to (2), wherein X is a chlorine atom.

(4) The process according to (2) or (3), wherein in a case that X is a chlorine atom, oxidation is carried out by a reaction with chlorine in a solvent essentially containing water.

(5) The process according to (1), wherein a compound represented by the following formula (11) is oxidized by means of an oxidizing agent essentially containing a halogen atom to obtain a compound represented by the following formula (1-A), and in a case that X in the compound represented by the formula (1-A) is a fluorine atom, such a compound is used as a compound represented by the formula (1F) wherein n is 2, and in a case that X is other than a fluorine atom, such X is converted into a fluorine atom, and the obtained compound is used as the compound represented by the formula (1F) wherein n is 2, provided that in the following formulae, $R^{A1}$ is a (2+m)valent organic group having at least two carbon atoms, and E, $R^B$, n, X and m are as defined above:

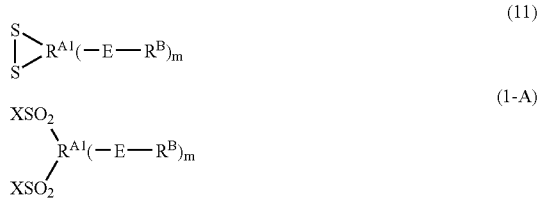

(6) The process according to any one of (1) to (5), wherein E is a —CH$_2$OCO— group (provided that the direction of the group is not restricted, and the carbon atom constituting the keto group is bonded to $R^A$, $R^{A1}$ or $R^B$), $E^F$ is a —CF$_2$OCO— group (provided that the direction of the group is the same direction corresponding to the direction of E, and the carbon atom constituting the keto group is bonded to $R^{AF}$ or $R^{BF}$), and $E^{F1}$ is a —COF group.

(7) The process according to any one of (1) to (6), wherein the compound represented by the formula (1F) is a compound having a fluorine content of at least 30 mass % and a molecular weight of from 200 to 1,300.

(8) The process according to any one of (1) to (7), wherein $R^A$ is a (n+m)valent saturated hydrocarbon group or a hetero atom-containing (n+m)valent saturated hydrocarbon group, $R^B$ is a perfluoro monovalent saturated hydrocarbon group, a perfluoro(partially halogeno monovalent saturated hydrocarbon) group, a perfluoro (hetero atom-containing monovalent saturated hydrocarbon) group or a perfluoro[partially halogeno (hetero atom-containing monovalent saturated hydrocarbon)] group, the compound represented by the formula (2) is a perfluorinated compound, $R^{AF}$ is a perfluoro (n+m)valent saturated hydrocarbon group or a perfluoro [hetero atom-containing (n+m)valent saturated hydrocarbon] group, and $R^{BF}$ is the same group as $R^B$.

(9) A process for producing a compound represented by the following formula (3a-1), which comprises oxidizing a compound represented by the formula (7-a) by reacting it with chlorine in a solvent essentially containing water to obtain a compound represented by the following formula (1-a), fluorinating the compound represented by the formula (1-a) to obtain a compound represented by the following formula (1F-a), reacting the compound represented by the formula (1F-a) with fluorine in a liquid phase to obtain a compound represented by the following formula (2-a), and carrying out a decomposition reaction of an ester bond in the compound represented by the formula (2-a):

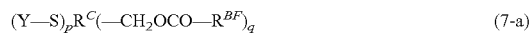
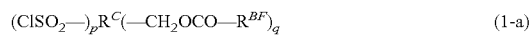
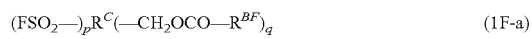
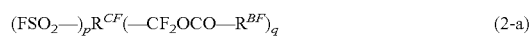

wherein Y is a hydrogen atom, a monovalent organic group or a —SO$_3^-$M$^+$ group (wherein M is an alkali metal atom), $R^C$ is a (p+q)valent organic group having at least two carbon atoms and containing no fluorine atom, $R^{CF}$ is a group having $R^C$ perfluorinated and represents a perfluorinated (p+q)valent organic group having at least two carbon atoms, $R^{BF}$ is a perfluorinated monovalent organic group, p is 2 or 3, and q is 1 or 2.

(10) A compound represented by the following formula (3a-1):

wherein $R^{CF}$ is a perfluorinated (p+q)valent organic group having at least two carbon atoms, p is 2 or 3, and q is 1 or 2.

(11) A compound represented by the following formula (3a-11):

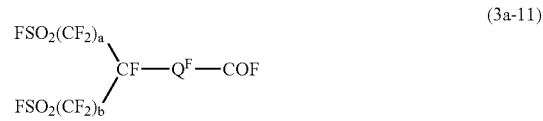

wherein a is an integer of from 1 to 3, b is an integer of from 1 to 3, and $Q^F$ is a single bond or a $C_{1-6}$ perfluoroalkylene group which may contain an etheric oxygen atom.

(12) A process for producing a compound represented by the following formula (12a), which comprises adding hexafluoropropylene oxide to a compound represented by the following formula (3a):

wherein $R^{AF}$ is the same group as $R^A$ or a (n+m)valent organic group having $R^A$ fluorinated, n is an integer of at least 2, and m is an integer of at least 1.

(13) A compound represented by the following formula (12a-1):

wherein $R^{CF}$ is a perfluorinated (p+q)valent organic group having at least two carbon atoms, p is 2 or 3, and q is 1 or 2.

(14) A compound represented by the following formula (12a-11):

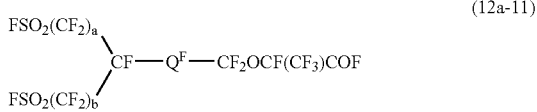

(12a-11)

wherein a is an integer of from 1 to 3, b is an integer of from 1 to 3, $Q^F$ is a single bond or a $C_{1-6}$ perfluoroalkylene group which may contain an etheric oxygen atom.

(15) A process for producing a fluorinated sulfonyl vinyl ether compound represented by the following formula (13b), which comprises subjecting a compound represented by the following formula (12a) to a pyrolytic reaction:

$$(FSO_2-)_nR^{AF}(-CF_2OCF(CF_3)COF)_m \quad (12a)$$

$$(FSO_2-)_nR^{AF}(-CF_2OCF=CF_2)_m \quad (13b)$$

wherein $R^{AF}$ is a perfluorinated (n+m)valent organic group, n is an integer of 2 or more, and m is an integer of 1 or more.

(16) A compound represented by the following formula (13a-1)

$$(FSO_2-)_pR^{CF}(-CF_2OCF=CF_2)_q \quad (13a-1)$$

wherein $R^{CF}$ is a perfluorinated (p+q)valent organic group having at least two carbon atoms, p is 2 or 3, and q is 1 or 2.

(17) A compound represented by the following formula (13b-11):

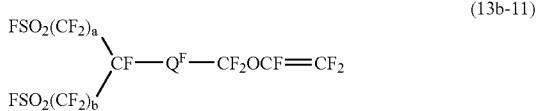

(13b-11)

wherein a is an integer of from 1 to 3, b is an integer of from 1 to 3, and $Q^F$ is a single bond or a $C_{1-6}$ perfluoroalkylene group which may contain an etheric oxygen atom.

BEST MODE FOR CARRYING OUT THE INVENTION

In this specification, the compound represented by the formula (1) will be referred to simply as "the compound 1". The compounds of other formulae will be referred to in the same manner.

In this specification, "an organic group" means a group containing at least one carbon atom. A "saturated" group means a group wherein carbon-carbon bonds are solely single bonds.

A "halogeno group" means a group having at least one hydrogen atom bonded to a carbon atom substituted by a halogen atom. A "perhalogeno group" means a group having substantially all of hydrogen atoms bonded to carbon atoms substituted by halogen atoms, and a "partially halogeno group" means a group having some of hydrogen atoms bonded to carbon atoms substituted by halogen atoms. In a case that the halogen atoms in such groups are specified to be fluorine atoms, they may be referred to as "perfluoro", "partially fluoro", etc. The same applies with respect to other halogen atoms.

The halogen atoms in the "perhalogeno" group and the "partially halogeno" group may be one type or two or more types. The "perhalogeno" group is preferably a group having all of hydrogen atoms bonded to carbon atoms substituted by halogen atoms. However, even when unsubstituted hydrogen atoms remain, so long as the nature as a group is substantially equal to a "perhalogeno" group, such a group will be included in the concept of the "perhalogeno" group in the present invention.

In the present invention, a "hetero atom-containing" group means a group containing hetero atom(s) such as oxygen atom(s), nitrogen atom(s) or sulfur atom(s), or hetero atom group(s) such as —C—C(O)—C— or —C—SO$_2$—C—. The hetero atom-containing group is preferably a group containing etheric oxygen atom(s) (—O—).

In the present invention, the "fluorination" means to introduce fluorine atoms into a compound. The fluorination is usually a reaction to substitute hydrogen atoms bonded to carbon atoms by fluorine atoms. In a case that an unsaturated bond is contained in an organic group, addition of fluorine atoms to the unsaturated bond is also included in the fluorination.

The production process of the present invention is a production process comprising a plurality of reaction steps. In the following description, in a case that a reaction product formed by a specific reaction step is used for the subsequent step, it may be used for the subsequent reaction or the like as it is, or purified in order that a reaction in the subsequent step will smoothly proceed. As a method for purifying such a crude reaction product, a method of distillating the crude reaction product as it is, a method of treating the crude reaction product with a diluted alkaline water or the like, followed by liquid separation, a method of extracting the crude reaction product with a proper organic solvent, followed by distillation, or silica gel column chromatography may, for example, be mentioned.

In the production process of the present invention, the starting material is a compound 1F. The compound 1F is a compound wherein a "n" number of fluorosulfonyl groups (FSO$_2$—) and a "m" number of groups represented by the formula -E-R$^B$ are bonded to a group represented by R$^A$. R$^A$ is a (n+m)valent organic group and is a group having at least two carbon atoms. R$^A$ has at least two, more preferably from 2 to 10 carbon atoms.

R$^A$ is preferably a (n+m)valent organic group essentially having C—H bond(s). Such an organic group is particularly preferably a (n+m)valent group having at least two carbon atoms, selected from a hydrocarbon group, a fluorohydrocarbon group, a hetero atom-containing hydrocarbon group and a fluoro(hetero atom-containing hydrocarbon) group. The hydrocarbon group moiety is preferably an aliphatic hydrocarbon group or an alicyclic hydrocarbon group, more preferably an aliphatic hydrocarbon group. The structure of the aliphatic hydrocarbon group may, for example, be a linear structure, a branched structure, a cyclic structure or a structure partially having a cyclic structure, and it is preferably a branched structure.

R$^A$ is preferably a saturated group containing no fluorine atom. Further, R$^A$ is particularly preferably a (n+m)valent group having at least two carbon atoms, which is a hetero atom-containing saturated hydrocarbon group, especially preferably a (n+m)valent group having at least two carbon atoms, which is a saturated hydrocarbon group containing an etheric oxygen atom.

In the compound 1F, n is an integer of 2 or more, and m is an integer of 1 or more n is preferably 2 or 3, and m is preferably 1 or 2. (n+m) is an integer of at least 3, preferably from 3 to 5, and in view of availability of the compound 1F, (n+m) is particularly preferably 3. Namely, R$^A$ is particularly preferably a trivalent organic group having at least two carbon atoms, especially preferably a trivalent organic group having at least two carbon atoms of which the organic group moiety is the above-mentioned preferred group. As a preferred example wherein $R^A$ is a trivalent saturated hydrocarbon group having at least two carbon atoms (containing an etheric oxygen atom), a group represented by the following formula (RA-1) may be mentioned (in the following formula, a is an integer of from 1 to 3, and b is an integer of from 1 to 3). As specific examples of such a group, groups as disclosed in the following specific examples of the compound 1F may be mentioned:

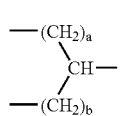
(RA-1)

$R^B$ is a monovalent organic group. $R^B$ has preferably from 1 to 20, especially preferably from 2 to 8 carbon atoms.

$R^B$ may, for example, be a monovalent hydrocarbon group, a halogeno monovalent hydrocarbon group, a hetero atom-containing monovalent hydrocarbon group or a halogeno(hetero atom-containing monovalent hydrocarbon) group. In such groups, the monovalent hydrocarbon moiety may be a monovalent aliphatic hydrocarbon group, a monovalent aromatic hydrocarbon group or a monovalent alicyclic hydrocarbon group, and is preferably a monovalent aliphatic hydrocarbon group. The monovalent aliphatic hydrocarbon moiety may have one or more unsaturated bonds, but such a moiety is preferably a saturated group. The structure of such a monovalent aliphatic hydrocarbon group may be a linear structure, a branched structure, a cyclic structure or a structure having a partially cyclic structure.

The $R^B$ moiety preferably has a fluorine atom, and $R^B$ is preferably a monovalent fluorinated organic group. Further, the monovalent fluorinated organic group is preferably a saturated group, more preferably a group having at least one hydrogen atom of a monovalent saturated hydrocarbon group substituted by a fluorine atom, or a group having at least one hydrogen atom of a hetero atom-containing monovalent saturated hydrocarbon group substituted by a fluorine atom. Further, $R^B$ is preferably a perfluoro (monovalent saturated hydrocarbon) group or a perfluoro(hetero atom-containing monovalent saturated hydrocarbon) group.

In a case that $R^B$ is a group containing a hetero atom, it is preferably a group containing an etheric oxygen atom from the viewpoint of availability, easiness of production and usefulness of a product. As specific examples of such $R^B$, a perfluoro(alkoxyalkyl) group and a perfluoro(alkoxy) group may be mentioned.

As specific examples of $R^B$, examples of $R^{B1}$ disclosed in the specific examples of the compound 1F as described hereinafter may be mentioned.

In the compound 1F, E is a bivalent connecting group. Further, E is also a group capable of forming $E^{F1}$ by a decomposition reaction carried out after a fluorination reaction as described hereinafter. E is preferably —CH$_2$OCO—. In a case that E is —CH$_2$OCO—, the direction of such a group is not restricted, and the carbon atom constituting the keto group may be bonded to $R^B$ or may be bonded to $R^A$. However, in the present invention, the carbon atom constituting the keto group in E is bonded preferably to $R^B$ from the reason of availability of the material compound.

As the compound 1F is a compound which reacts with fluorine in a liquid phase, it is a compound in which a structure capable of being fluorinated is present. Namely, at least one of $R^A$, $R^B$ and E is a group capable of being fluorinated. It is preferred that $R^A$ and/or E is a group capable of being fluorinated and $R^B$ is a perfluorinated monovalent organic group, and it is particularly preferred that $R^A$ and E are groups capable of being fluorinated and $R^B$ is a perfluorinated monovalent organic group. In a case that $R^B$ is a perfluorinated monovalent organic group, $R^{BF}$ as described hereinafter and $R^B$ are the same groups.

As specific examples of the compound 1F, the following compounds may be mentioned. In the following formulae, $R^{B1}$ is —(CF$_2$)$_s$F (wherein s is an integer of from 1 to 20, preferably from 2 to 5), —CF(CF$_3$)$_2$, —CF(CF$_3$)O(CF$_2$)$_3$F or —CF(CF$_3$)OCF$_2$CF(CF$_3$)O(CF$_2$)$_3$F:

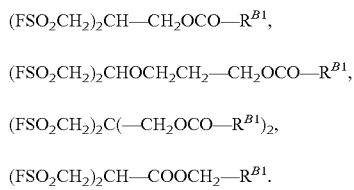

A method to obtain the compound 1F in the present invention will be described hereinafter.

In the present invention, the compound 1F is fluorinated to obtain a compound 2.

The fluorination reaction is carried out by a liquid phase fluorination method of reaction with fluorine (F$_2$) in a liquid phase. The fluorination method by a liquid phase fluorination method is remarkably advantageous from the viewpoint of the efficiency in the reaction operation and the yield, as compared with a cobalt fluorination method or an electrochemical fluorination method.

As a means of the liquid phase fluorination method, a known method may be applied. In order that the liquid phase fluorination proceeds advantageously, the fluorine content of the compound 1F is preferably at least 30 mass %, particularly preferably from 30 to 86 mass %, especially preferably from 30 to 76 mass %. Further, the molecular weight of the compound 1F is preferably from 200 to 1,300. As the fluorine, fluorine gas may be employed as it is, or fluorine gas diluted with an inert gas may be employed. As such an inert gas, nitrogen gas is preferred.

In a case that the fluorine gas diluted with an inert gas is employed, the amount of the fluorine gas is at least 10 vol % based on the total amount of the inert gas and fluorine from the viewpoint of the efficiency, and it is particularly preferably at least 20 vol %.

The liquid phase fluorination is carried out preferably in the presence of a solvent. As such a solvent, a known solvent which can be used for a liquid phase fluorination may be employed. The solvent is preferably a solvent which is capable of dissolving at least 1 mass % of the compound 1F, particularly preferably a solvent capable of dissolving at least 5 mass % of the compound 1F. Examples of the solvent include solvents exemplified in the fluorination step in WO02/44138. The amount of the solvent to the compound 1F is preferably at least five times by mass, particularly preferably from 10 to 100 times by mass.

The fluorination reaction is carried out preferably in a batch system, a continuous system or the like. When the reaction is carried out in such a system, the reaction manner as disclosed in WO02/44138 will be applicable.

The amount of fluorine to be used for the fluorination reaction is preferably in an excess amount relative to the hydrogen atoms to be fluorinated. In the fluorination reaction, it is preferred to maintain such an excess amount state from the initiation to the termination of the reaction. For example, the amount of fluorine is preferably at least 1.5 times by mol relative to the hydrogen atoms to be fluorinated, from the viewpoint of the selectivity.

The reaction temperature for the fluorination reaction is usually preferably −60° C. or higher, and particularly preferably from −50° C. to +100° C. from the viewpoint of the reaction yield, the selectivity and the efficiency for industrial operation, especially preferably from −20° C. to +50° C. The reaction pressure for the fluorination reaction is preferably from normal pressure to 2 MPa (gage pressure, the same applies hereinafter) from the viewpoint of the reaction yield, the selectivity and the efficiency for industrial operation.

In the fluorination reaction, a C—H bond-containing compound may be reacted to the reaction system at a latter stage of the reaction, and/or ultraviolet irradiation may be carried out. As a specific method, methods as disclosed in WO02/44138 may be employed.

In the fluorination reaction of the present invention, a compound 2 will be formed. In the compound 2, $R^{AF}$ is a group corresponding to $R^A$, and is the same group as $R^A$ or a (n+m)valent organic group having $R^A$ fluorinated. In a case that $R^A$ is a group incapable of being fluorinated, or in a case that it is a group capable of being fluorinated but is not fluorinated, $R^{AF}$ and $R^A$ are the same groups. In the present invention, $R^A$ is preferably a (n+m)valent non-fluorinated organic group having at least two carbon atoms, capable of being fluorinated, and $R^{AF}$ is preferably a (n+m)valent perfluoro organic group having at least two carbon atoms, having $R^A$ perfluorinated.

$E^F$ is a group corresponding to E, and is the same group as E or a bivalent connecting group having E fluorinated. In a case that E is a group incapable of being fluorinated, or in a case that it is a group capable of being fluorinated but is not fluorinated, $E^F$ is the same group as E. E is preferably a bivalent connecting group capable of being fluorinated, which is a group containing no fluorine atom, and $E^F$ is preferably a bivalent connecting group having E perfluorinated.

$R^{BF}$ is a group corresponding to $R^B$, and is the same group as $R^B$ or a monovalent organic group having $R^B$ fluorinated. In a case that $R^B$ is a group incapable of being fluorinated, or in a case that it is a group capable of being fluorinated but is not fluorinated, $R^{BF}$ is the same as $R^B$. $R^B$ and $R^{BF}$ are preferably the same perfluorinated monovalent organic groups.

In the compound 2, the numbers of n and m are respectively the same numbers corresponding to n and m in the compound 1F, and their preferred embodiments are also the same.

The compound 2 may be a partially fluorinated compound, but is preferably a perfluorinated compound from the viewpoint of the usefulness of an aimed compound. Namely, the fluorination of the compound 1F is preferably a reaction of perfluorinating the compound 1F.

In a case that the compound 2 is a perfluorinated compound, $R^{AF}$ is preferably a group having all C—H moiety(ies) of $R^A$ which is a (n+m)valent organic group essentially containing C—H bond(s), substituted by fluorine atom(s), particularly preferably a perfluoro (n+m)valent saturated hydrocarbon group or a perfluoro[hetero atom-containing (n+m)valent saturated hydrocarbon)] group. As specific examples of $R^{AF}$, groups as disclosed in specific examples of the compound 2 may be mentioned.

Further, in a case that E is —CH$_2$OCO—, $E^F$ is preferably —CF$_2$OCO—. The carbon atom constituting the keto group in such a group may be bonded to $R^{AF}$ or may be bonded to $R^{BF}$, and its direction corresponds to the direction of E.

In a case that $R^B$ is a perfluorinated monovalent group, $R^{BF}$ and $R^B$ are the same groups. $R^{BF}$ is preferably a perfluoro monovalent saturated hydrocarbon group, a perfluoro(partially-halogeno monovalent saturated hydrocarbon) group, a perfluoro(hetero atom-containing monovalent saturated hydrocarbon) group or a perfluoro[partially halogeno(hetero atom-containing monovalent saturated hydrocarbon)] group.

The compound 2 is preferably the following compound (2-a). In the following formula, $R^{CF}$ is a perfluorinated (p+q)valent (i.e. trivalent to pentavalent) organic group having at least two carbon atoms, p is 2 or 3, and q is 1 or 2:

$$(FSO_2—)_p R^{CF}(—CF_2OCO—R^{BF})_q \tag{2-a}$$

As specific examples of the compound 2, the following compounds may be mentioned. In the following formulae, $R^{BF1}$ is —(CF$_2$)$_s$F (wherein s is an integer of from 1 to 20, preferably from 2 to 5), —CF(CF$_3$)$_2$, —CF(CF$_3$)OCF$_2$CF$_3$ or —CF(CF$_3$)OCF$_2$CF(CF$_3$)OCF$_2$CF$_2$CF$_3$:

(FSO$_2$—CF$_2$)$_2$CF—CF$_2$OCO—R$^{BF1}$, (FSO$_2$—CF$_2$)$_2$CFOCF$_2$CF$_2$—CF$_2$OCO—R$^{BF1}$, (FSO$_2$—CF$_2$)$_2$C(—CF$_2$OCO—R$^{BF1}$)$_2$, (FSO$_2$—CF$_2$)$_2$CF—COOCF$_2$—R$^{BF1}$.

In the present invention, the compound 2 is decomposed to obtain a compound 3. The means of the decomposition reaction may suitably be changed depending upon the type of $E^F$. For example, in a case that $E^F$ is —CF$_2$OCO—, a known means for a decomposition reaction of an ester bond may be employed.

The decomposition reaction of an ester bond is carried out preferably by a gas phase reaction or a liquid phase reaction. In a case that the boiling point of the compound 2 is low, it is carried out preferably by a gas phase reaction. In a case that the reaction is carried out by a gas phase reaction, the reaction temperature is preferably from 50 to 350° C., particularly preferably from 50 to 300° C., especially preferably from 150 to 250° C. The reaction may be carried out in the presence of an inert gas which is not directly involved in the reaction. Such an inert gas may, for example, be nitrogen gas or carbon dioxide gas. In a case that an inert gas is employed, it is used preferably in an amount of from about 0.01 to about 50 vol % based on the compound 2. If the amount of the inert gas added is too large, the amount of the product to be recovered may be reduced in some cases.

In a case that the compound 2 is hardly vaporizable, the decomposition reaction of an ester bond is carried out preferably in a liquid phase reaction. The liquid phase reaction is preferably by a method of heating the compound 2 as it is in a liquid form in a reactor. In a case of a liquid phase reaction, the reaction temperature is preferably from 50 to 300° C., particularly preferably from 100 to 250° C.

The reaction pressure in the liquid phase reaction is not limited. Further, the reaction may be carried out in such a manner that the decomposition reaction of the compound 2 is carried out employing a reactor equipped with a distillation column, while continuously discharging the product of the decomposition reaction from the reaction system.

In a case that the decomposition reaction of an ester bond is carried out by a liquid phase reaction, it may be carried out in the presence of a solvent or in the absence of a solvent. In a case that a solvent is employed, preferred is an inert solvent such as a perfluorotrialkylamine or perfluoronaphthalene or a high boiling chlorofluorocarbon such as a chlorotrifluoroethylene oligomer. The amount of the solvent is preferably from 10 to 1,000 mass % based on the compound 2.

In a case that the decomposition reaction of an ester bond is carried out in a liquid phase reaction, it may be carried out by a reaction with a nucleophilic agent or an electrophilic agent. The nucleophilic agent is preferably $F^-$, particularly preferably $F^-$ derived from an alkali metal fluoride (for example, NaF, $NaHF_2$, KF, CsF or the like may be mentioned, and NaF and KF are preferred from the viewpoint of the economical efficiency and the reactivity). The amount of the nucleophilic agent may be in a catalytic amount or in an excess amount, and it is preferably from 1 to 500 mol %, particularly preferably from 1 to 100 mol %, especially preferably from 5 to 50 mol %, based on the compound 2. In a case that a nucleophilic agent or an electrophilic agent is employed, the reaction temperature is preferably from $-30°$ C. to $250°$ C., particularly preferably from $-20°$ C. to $250°$ C.

By the decomposition reaction of the compound 2, the compound 3 will be formed. In the compound 3, $R^{AF}$, m and n are the same as in the compound 2 used for the reaction, and $E^{F1}$ is a monovalent group formed by the decomposition reaction of $E^F$. The structure of $E^{F1}$ varies depending upon the structure of $E^F$ and the type of the decomposition reaction. For example, in a case that $E^F$ is $—CF_2OCO—$ and the decomposition reaction is a decomposition reaction of an ester bond, $E^{F1}$ is not limited to the direction of the group $E^F$ and is a $—COF$ group.

The compound 3 is preferably the following compound (3a-1) (in the following formula, p, q and $R^{CF}$ are as defined above):

$$(FSO_2—)_pR^{CF}(—COF)_q \quad (3a\text{-}1)$$

As specific examples of the compound 3, the following compounds may be mentioned:

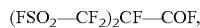

$$(FSO_2—CF_2)_2CF—COF,$$

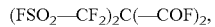

$$(FSO_2—CF_2)_2C(—COF)_2,$$

$$(FSO_2—CF_2)_2CFOCF_2CF_2—COF.$$

The compound 3 is a compound useful as e.g. a starting material of a monomer for an ion-exchange resin. Specific examples of conversion of the compound 3 into a useful compound will be described hereinafter.

A method to obtain the compound 1F as a starting material in the production process of the present invention is not particularly limited, and a method of employing a commercial product, or a method of producing the compound 1F employing a known compound as a material may, for example, be mentioned.

In a case that the compound 1F is obtained by the latter method, production by the following Production Process 1, 2 or 3 is particularly preferred since a variety of the compounds 1F will be obtained. In the following description, X, $R^A$, E, $R^B$, n and m are as defined above. $E^1$ is a monovalent reactive group, and $E^2$ is a monovalent reactive group capable of forming the above E by reaction with the above $E^1$. Z is a halogen atom, an alkyl sulfonyloxy group or an aryl sulfonyloxy group. Y is a hydrogen atom, a monovalent organic group or a $—SO_3^-M^+$ group (wherein M is an alkali metal atom). $R^{A1}$ is a (2+m)valent organic group having at least two carbon atoms.

Process 1 for Production of Compound 1

The following compound 7 is oxidized by means of an oxidizing agent essentially containing a halogen atom to form the following compound 1, whereby a compound 1F wherein X is a fluorine atom is obtained. On the other hand, in a case that a compound 1 wherein X is a halogen atom other than a fluorine atom is obtained, such X is converted into a fluorine atom to obtain the compound 1F. X in the compound 1 corresponds to the type of the halogen atom in the oxidizing agent used:

$$(Y—S—)_nR^A(\text{-}E\text{-}R^B)_m \quad (7)$$

$$(XSO_2—)_nR^A(\text{-}E\text{-}R^B) \quad (1)$$

In the Production Process 1, the Y—S— group in the compound 7 is converted into a $X—SO_2—$ group. The method of the oxidation reaction may optionally be changed depending upon the type of X in such a group.

For example, in a case of forming the compound 1F wherein X is a fluorine atom, preferred is a method of reacting hydrofluoric acid and nitrogen dioxide with the compound 7.

In a case of forming the compound 1 wherein X is a halogen atom other than a fluorine atom (hereinafter such a halogen atom will be referred to as another halogen atom and represented by $X^1$), a method of a reaction with another halogen (($X^1)_2$) in a solvent essentially containing water may be mentioned.

The Production Process 1 is preferably a process via another halogen. The compound 1 wherein X is another halogen atom, is a compound wherein X is a chlorine atom, a bromine atom or an iodine atom. Such a process is a process particularly preferred when Y in the compound 7 is a $R^aOC(=S)—$ group (wherein $R^a$ is an alkyl group), a cyano group or a benzyl group, which is a preferred group as mentioned hereinafter. $X^1$ is preferably a chlorine atom. Namely, it is preferred to obtain a compound 1 wherein X is a chlorine atom and then convert the chlorine atom in the compound 1 into a fluorine atom.

The process to form the compound 1 wherein X is a chlorine atom is preferably a process of reacting the compound 7 with chlorine ($Cl_2$) in a solvent essentially containing water. Such a process is preferably a process of reacting the following compound (7-a) with chlorine in a solvent essentially containing water to form the following compound (1-a). In the following formulae, p, q, Y and $R^{BF}$ are as defined above. $R^C$ is as defined above, and is preferably a (p+q)valent organic group having from 2 to 16 carbon atoms and containing no fluorine atom:

$$(Y—S)_pR^C(—CH_2OCO—R^{BF})_q \quad (7\text{-}a)$$

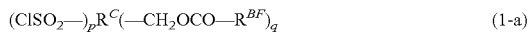

$$(ClSO_2—)_pR^C(—CH_2OCO—R^{BF})_q \quad (1\text{-}a)$$

Further, in a case of forming a compound 1 wherein X is a bromine atom, preferred is a process of reacting the compound 7 with bromine ($Br_2$) in a solvent essentially containing water. Such a process may be carried out in accordance with a known means (New Experimental Chemistry, The Chemical Society of Japan, Maruzen Company, Limited, Tokyo, 1978, Vol. 14 (Syntheses and Reactions of Organic Compounds (III)), pages 1,785 to 1,786, etc.).

In a case of carrying out a reaction with chlorine, a method of employing chlorine gas or a method of employing chlorine gas diluted with an inert gas may be mentioned. The inert gas is preferably nitrogen gas or helium gas, particularly preferably nitrogen gas. In a case of employing an inert gas, the amount of the chlorine gas based on the total amount of the inert gas and the chlorine gas is preferably at least 10 vol % in view of efficiency, particularly preferably at least 20 vol %.

The solvent essentially containing water is preferably water, a mixed solvent of water with acetic acid or a mixed solvent of water with acetonitrile. The amount of such a solvent is preferably at least two times by mass, particularly preferably from 5 to 50 times by mass, to the compound 7. The amount of water is preferably from 4 to 2,000 times by mol, particularly preferably from 20 to 1,000 times by mol, to the compound 7.

The reaction temperature in the reaction of the compound 7 with another halogen is usually preferably $-20°$ C. or higher, and preferably from $0°$ C. to $+60°$ C. in view of the reaction yield, the selectivity and the efficiency for industrial operation. The reaction pressure in the chlorination reaction is preferably from normal pressure to 2 MPa in view of the reaction yield, the selectivity and the efficiency for industrial operation.

In a case that $X^1$ is another halogen atom, X is converted into a fluorine atom to form the compound 1F. This is because the yield will remarkably decrease if liquid phase fluorination is carried out employing the compound 1 wherein X is another halogen atom. The yield will remarkably be improved when fluorination is carried out after X is substituted by a fluorine atom.

As a method of substituting another halogen atom ($X^1$) in the compound 1 by a fluorine atom, a known means may be employed. For example, a method for reacting the compound 1 with potassium fluoride or potassium hydrogen fluoride in a solvent may be mentioned (Scott R. B., Gordon M. J., J. Org. Chem., 1956, 21, p. 385, Gramstad T., Hazeldine R. N., J. Chem. Soc., 1956, p. 173).

The solvent in such a method is preferably a mixed solvent of water with dioxane, or a mixed solvent of water with acetonitrile. The amount of the solvent to the compound 1 is preferably at least two times by mass, particularly preferably from 5 to 50 times by mass. The reaction temperature in such a reaction is usually preferably from $-20°$ C. to the boiling point of the solvent, and from the viewpoint of the reaction yield, the selectivity and the efficiency for industrial operation, it is particularly preferably from $0°$ C. to $+60°$ C. The reaction pressure for the reaction is particularly preferably from normal pressure to 2 MPa from the viewpoint of the reaction yield, the selectivity and the efficiency for industrial operation.

The method is preferably a method of converting the compound (1-a) into the following compound (1F-a) (in the following formula, p, q, $R^C$ and $R^{BF}$ are as defined above):

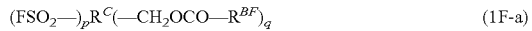

(1F-a)

Process 2 for Production of Compound 1

This process is a process to obtain a compound 1 wherein n is 2 (i.e. the following compound 1F-A). That is, a compound 10 and "m" molecules of a compound 5 represented by the formula $R^B$-$E^2$ are reacted to obtain a compound 11, and the compound 11 is oxidized by means of an oxidizing agent essentially containing a halogen atom to obtain a compound 1-A.

A compound wherein X in the compound 1-A is a fluorine atom, is a compound 1F-A. In a case that X in the compound 1-A is another halogen atom, X is converted into a fluorine atom to obtain a compound 1F-A:

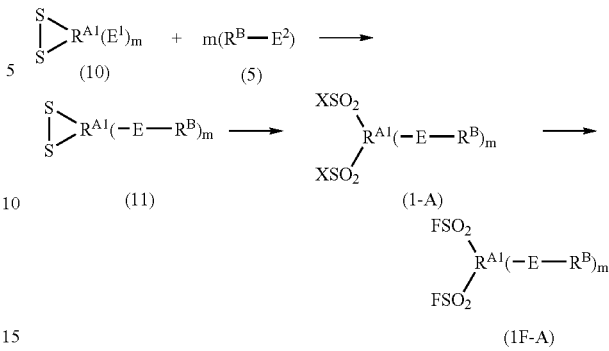

The compound 10 in the Production Process 2 is a compound essentially containing a monovalent cyclic structure essentially containing a disulfide bond. $R^{41}$ is a (2+m) valent organic group having at least two carbon atoms, preferably a trivalent organic group having three carbon atoms, particularly preferably a trivalent saturated aliphatic hydrocarbon group having three carbon atoms. That is, the monovalent cyclic structure essentially containing a disulfide bond is preferably a 5-membered cyclic structure.

In the compound 10 and the compound 5, $E^1$ and $E^2$ are the same groups as those groups in a Process 1-1 for Production of Compound 7 as described hereinafter, and their preferred embodiments are also the same. Further, one of $E^1$ and $E^2$ is —COW (wherein W is the same as W in Process 1-1 for Production of Compound 7 as described hereinafter), and the other is —CH$_2$OH. In a case that E is —CH$_2$OCO—, the reaction of the compound 10 with the compound 5 is an esterification reaction, and such a reaction may be carried out in the same manner as in an esterification reaction of a compound 4 with a compound 5 in the Process 1-1 for Production of Compound 7 as described hereinafter.

Further, the oxidation reaction of the compound 11 may be carried out in the same manner as in the oxidation reaction of the compound 7 in the Production Process 1. In the oxidation reaction of the compound 11, the disulfide bond undergoes cleavage to form two XSO$_2$-groups.

Process 3 for Production of Compound 1

A process of reacting the following compound 9 with the following compound 5 to obtain the compound 1F:

 (9)

 (5)

In the compound 9 and the compound 5, $E^1$ and $E^2$ are the same groups as those in the Process 1-1 for Production of Compound 7 as described hereinafter, and their preferred embodiments are also the same. Further, one of $E^1$ and $E^2$ is —COW (wherein W is the same as W in the Process 1-1 for Production of Compound 7 as described hereinafter), and the other is —CH$_2$OH. In a case that E is —CH$_2$OCO—, the reaction of the compound 9 with the compound 5 is an esterification reaction, and such a reaction may be carried out in the same manner as in an esterification reaction of a compound 4 with a compound 5 as described hereinafter.

The compound 7 in the above Production Process 1 is preferably a compound 7 obtained by the process as described in the following Production Process 1-1 or Production Process 1-2.

Process 1-1 for Production of Compound 7

A process of reacting the following compound 4 with the following compound 5 to obtain a compound 6 and reacting the compound 6 with a sulfur nucleophile to obtain the following compound 7:

(4)

(5)

(6)

(7)

In the compound 4, Z is a halogen atom, an alkyl sulfonyloxy group or an aryl sulfonyloxy group, and in a case that Z is a halogen atom, it is preferably a chlorine atom or a bromine atom. In a case that Z is an alkyl sulfonyloxy group, preferred is such a group having from 1 to 6 carbon atoms. In a case that Z is an aryl sulfonyloxy group, preferred is such a group having from 6 to 10 carbon atoms. Further, in a case that Z is an alkyl sulfonyloxy group or an aryl sulfonyloxy group, the hydrogen atom at the C—H moiety may be substituted by a substituent.

In the compound 4, Z is preferably a chlorine atom, a bromine atom, a methane sulfonyloxy group, a trifluoromethane sulfonyloxy group, a benzene sulfonyloxy group or a toluene sulfonyloxy group, particularly preferably a bromine atom.

Further, it is preferred that one of $E^1$ and $E^2$ is —COW (wherein W is a halogen atom or a hydroxyl group) and the other is —CH$_2$OH, and that E is —CH$_2$OCO— (provided that the carbon atom constituting the keto group in E is bonded to $R^A$ or $R^B$). In a case that one of $E^1$ and $E^2$ is —COW and the other is —CH$_2$OH, the reaction of the compound 4 with the compound 5 may be carried out under conditions for known esterification reactions. The esterification reaction may be carried out in the presence or absence of a solvent, and it is carried out preferably in the absence of a solvent. Further, in the esterification reaction, in a case that W is a halogen atom, an acid represented by HW will form, and accordingly it is preferred to carry out such an operation that an acid scavenger is made to present in the reaction system, or the acid is let to accompany a nitrogen stream and be discharged out of the reaction system. For example, in a case that W is a fluorine S atom, as a scavenger of HF, an alkali metal fluoride such as NaF or KF may be mentioned. In the esterification reaction, in a case that W is a hydroxyl group, it is preferred that a dehydrating agent is present in the reaction system, whereby progress of the reaction will be accelerated. The dehydrating agent is preferably trifluoroacetic anhydride, thionylchloride or the like. The amount of the dehydrating agent is preferably from 1 to 10 times by mol to the theoretical amount of water to be formed.

The reaction temperature for the esterification reaction of the compound 4 with the compound 5 is preferably −50° C. or higher, more preferably from −50° C. to +100° C. The reaction time may suitably be changed depending upon the supply rate of the materials and the amount of the compounds to be used for the reaction. The reaction pressure is preferably from normal pressure to 2 MPa.

The compound 6 formed by the esterification reaction is then reacted with a sulfur nucleophile to obtain the compound 7. The compound 7 is a compound wherein the Z moiety in the compound 6 is converted into a Y—S-moiety. Y is a hydrogen atom, a monovalent organic group or a —SO$_3^+$M$^-$ group (wherein M is an alkali metal atom), and the structure of the Y—S-moiety corresponds to the type of the sulfur nucleophile to be used for the reaction.

In a case that Y is a monovalent organic group, it is preferably a $R^aOC(=S)$— group (wherein $R^a$ is an alkyl group), a $(R^b)_2NC(=S)$— group (wherein $R^b$ is an alkyl group), a cyano group, a benzyl group or a —C$^+$(NH$_2$)$_2$Z$^-$ group (wherein Z corresponds to Z in the formula (6) as described hereinafter and represents a halogen atom, an alkyl sulfonyloxy group or an aryl sulfonyloxy group).

The sulfur nucleophile to obtain a compound 7 wherein Y is a hydrogen atom, is preferably a metal sulfide (such as a compound represented by the formula M$^1$SH, wherein M$^1$ is an alkali metal atom).

In a case that a compound 7 wherein Y is a monovalent organic group is to be obtained, it is preferred to employ the following sulfur nucleophile depending upon the type of the monovalent organic group (Y).

For example, as an example to obtain a compound 7 wherein Y is a $R^aOC(=S)$— group (wherein $R^a$ is an alkyl group), preferred is an O-alkyldithiocarbonate (such as a compound represented by the formula $R^aOC(=S)SM^2$, wherein $R^a$ is as defined above, and $M^2$ is an alkali metal atom). As an example to obtain a compound 7 wherein Y is a $(R^b)_2NC(=S)$— group (wherein $R^b$ is an alkyl group), preferred is a N,N-dialkyldithiocarbamate (such as a compound represented by $(R^b)_2NC(=S)SM^3$, wherein $R^b$ is as defined above, and $M^3$ is an alkali metal atom). As an example to obtain a compound 7 wherein Y is a cyano group, preferred is a thiocyanate (such as a compound represented by M$^4$SCN, wherein M$^4$ is an alkali metal atom). As an example to obtain a compound 7 wherein Y is a benzyl group, preferred is benzyl mercaptan (C$_6$H$_5$CH$_2$SH). As an example to obtain a compound 7 wherein Y is —C$^+$(NH$_2$)$_2$Z$^-$ group (wherein Z corresponds to Z in the formula (6), and Z is as defined above), preferred is thiourea (such as a compound represented by H$_2$NC(=S)NH$_2$).

As the sulfur nucleophile to obtain a compound 7 wherein Y is —SO$_3$M (wherein M is an alkali metal atom), preferred is a thiosulfate (such as a compound represented by the formula MO—SO(=S)—OM, wherein M is as defined above).

Among them, the sulfur nucleophilic agent is particularly preferably an O-alkyldithiocarbonate, a thiocyanate or a benzyl mercaptan, and Y corresponding to the sulfur nucleophilic agent is preferably a $R^aOC(=S)$— group (wherein $R^a$ is as defined above), a cyano group or a benzyl group.

The reaction with the sulfur nucleophilic agent may be carried out in accordance with a known method (New Experimental Chemistry (The Chemical Society of Japan), Maruzen Company, Limited, Tokyo, 1978, Vol. 14, pages 1701 to 1706). Further, it is preferred to react the compound 6 wherein Z is a halogen atom with a thiocyanate to obtain the compound 7 wherein Y is CN.

The reaction with the sulfur nucleophile is carried out preferably in the presence of a solvent. The solvent is preferably water, ethanol, acetone or N,N-dimethylacetamide. The amount of the solvent is preferably from 50 to 500 mass % based on the total amount of the compound 6 and the sulfur nucleophile.

The temperature for the reaction with the sulfur nucleophile is preferably from 0° C. to +100° C. Further, the reaction time may suitably be changed depending upon the supply rate of the materials and the amounts of the compounds to be used for the reaction. The pressure for the reaction is preferably from normal pressure to 2 MPa.

Process 1-2 for Production of Compound 7

A process of reacting the following compound 8 with the following compound 5 to obtain a compound 7:

$$(Y-S-)_n R^A(-E^1)_m \quad (8)$$

$$R^B-E^2 \quad (5)$$

$$(Y-S-)_n R^A(-E-R^B)_m \quad (7)$$

In the compound 8 and the compound 5, Y, $E^1$ and $E^2$ are the same groups as those in Process 1-1 for Production of Compound 7, and their preferred embodiments are also the same. Further, one of $E^1$ and $E^2$ is —COW (wherein W is as defined above), and the other is —CH$_2$OH. In a case that E is —CH$_2$OCO—, the reaction of the compound 8 with the compound 5 is an esterification reaction, and such a reaction may be carried out in the same manner as the esterification reaction of the compound 4 and the compound 5.

In Processes 1 to 3 for Production of Compound 1 and Processes 1-1 and 1-2 for Production of Compound 7, as specific examples of the respective compounds, the following examples may be mentioned.

As examples wherein X in the compound 1 is a chlorine atom, an iodine atom or a bromine atom, examples wherein the fluorine atom in the FSO$_2$— group in specific examples of the compound 1F is changed to a chlorine atom, an iodine atom or a bromine atom, may be mentioned.

Specific examples of the compound 4:

(BrCH$_2$)$_2$CH—CH$_2$OH, (BrCH$_2$)$_2$C(—CH$_2$OH)$_2$, (ClCH$_2$)$_2$CHOCH$_2$CH$_2$—CH$_2$OH, (BrCH$_2$)$_2$CH—COOH, (BrCH$_2$)$_2$CH—COCl.

Specific examples of the compound 5 (wherein $R^B$ is as defined above):

$R^B$COF, $R^B$CH$_2$OH.

Specific examples of the compound 6 (wherein $R^B$ is as defined above):

(BrCH$_2$)$_2$CHCH$_2$OCOR$^B$, (BrCH$_2$)$_2$C(CH$_2$OCOR$^B$)$_2$, (ClCH$_2$)$_2$CHOCH$_2$CH$_2$CH$_2$OCOR$^B$, (BrCH$_2$)$_2$CHCOOCH$_2$R$^B$.

Specific examples of the compound 7 (wherein $R^B$ is as defined above):

(NCSCH$_2$)$_2$CHCH$_2$OCOR$^B$, (CH$_3$CH$_2$OCSSCH$_2$)$_2$CHCH$_2$OCOR$^B$, (NCSCH$_2$)$_2$C(—CH$_2$OCOR$^B$)$_2$, (CH$_3$CH$_2$OCSSCH$_2$)$_2$C(—CH$_2$OCOR$^B$)$_2$, (C$_6$H$_5$CH$_2$SCH$_2$)$_2$CHOCH$_2$CH$_2$CH$_2$OCOR$^8$, (NCSCH$_2$)$_2$CHCOOCH$_2$R$^B$, (CH$_3$CH$_2$OCSSCH$_2$)$_2$CHCOOCH$_2$R$^B$, (C$_6$H$_5$CH$_2$SCH$_2$)$_2$CHCH$_2$OCOR$^B$, (C$_6$H$_5$CH$_2$SCH$_2$)$_2$C(—CH$_2$OCOR$^B$)$_2$, (C$_6$H$_5$CH$_2$SCH$_2$)$_2$CHCOOCH$_2$R$^B$.

Specific examples of the compound 8:

(NCSCH$_2$)$_2$CHCH$_2$OH, (NCSCH$_2$)$_2$C(CH$_2$OH)$_2$, (CH$_3$CH$_2$OCSSCH$_2$)$_2$CHCH$_2$OH, (CH$_3$CH$_2$OCSSCH$_2$)$_2$C(—CH$_2$OH)$_2$, (C$_6$H$_5$CH$_2$SCH$_2$)$_2$CHOCH$_2$CH$_2$OH, (NCSCH$_2$)$_2$CHCOOH, (CH$_3$CH$_2$CSSCH$_2$)$_2$CHCOOH, (C$_6$H$_5$CH$_2$SCH$_2$)$_2$CHCH$_2$OH, (C$_6$H$_5$CH$_2$SCH$_2$)$_2$C(CH$_2$OH)$_2$, (NCSCH$_2$)$_2$CHCOOH.

Specific examples of the compound 9:

(FSO$_2$CH$_2$)$_2$CHCH$_2$OH, (FSO$_2$CH$_2$)$_2$C(CH$_2$OH)$_2$, (FSO$_2$CH$_2$)$_2$CHOCH$_2$CH$_2$CH$_2$OH.

Specific examples of the compound 10:

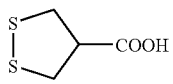 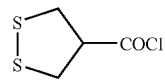

Specific example of the compound 11 (wherein $R^{B1}$ is as defined above):

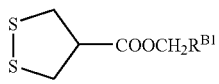

The production process of the present invention is preferably a production process wherein E is —CH$_2$OCO—, and $E^F$ is —CF$_2$OCO—.

That is, preferred is a process for producing the following compound 3a, which comprises, in a case that X in the following compound 1a is a fluorine atom, reacting the compound 1a with fluorine in a liquid phase as it is to form the following compound 2a, and in a case that X is a halogen atom other than a fluorine atom, converting such X into a fluorine atom and then reacting the obtained compound with fluorine in a liquid phase to form the following compound 2a, and decomposing the compound 2a.

Further, preferred is a process for producing the following compound 3a, which comprises, in a case that X in the following compound 1b is a fluorine atom, reacting the compound 1b with fluorine in a liquid phase as it is to form the following compound 2b, and in a case that X is a halogen atom other than a fluorine atom, converting such X into a fluorine atom and then reacting the obtained compound with fluorine in a liquid phase to form the following compound 2b, and decomposing the compound 2b.

In the following formulae, the symbols are as defined above, and their preferred embodiments are also the same.

$$(XSO_2—)_n R^A(—CH_2OCO—R^B)_m \quad (1a)$$

$$(FSO_2—)_n R^{AF}(—CF_2OCO—R^{BF})_m \quad (2a)$$

$$(FSO_2—)_n R^{AF}(COF)_m \quad (3a)$$

$$(XSO_2—)_n R^A(—COOCH_2—R^B)_m \quad (1b)$$

$$(FSO_2—)_n R^{AF}(—COOCF_2—R^{BF})_m \quad (2b)$$

The compound (3a) is preferably the following compound 3a-1 wherein n is 2 or 3 and m is 1 or 2. In the following formula, $R^{CF}$ is a perfluorinated (p+q)valent (i.e. trivalent to pentavalent) organic group having at least two carbon atoms. $R^{CF}$ is preferably a perfluorinated (p+q)valent organic group having from 2 to 16 carbon atoms p is 2 or 3 and q is 1 or 2:

$$(FSO_2—)_p R^{CF}(—COF)_q \quad (3a-1)$$

$R^{CF}$ is preferably a perfluoro(trivalent organic group) having at least two carbon atoms. Such a perfluoro(trivalent organic group) is preferably a perfluoro(trivalent saturated hydrocarbon group) or a perfluoro(etheric oxygen atom-containing trivalent saturated hydrocarbon group).

The compound (3a-1) is preferably the following compound (3a-11) (in the following formula, a, b and $Q^F$ are as defined above):

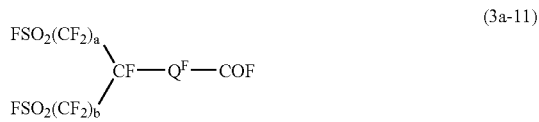

(3a-11)

a and b are preferably the same. Each of a and b is preferably an integer of from 1 to 3, particularly preferably 1 or 2. $Q^F$ is preferably a single bond or a $C_{1-6}$ perfluoroalkylene group containing an etheric oxygen atom, particularly preferably a $C_{1-6}$ perfluoro(oxyalkylene) group having an etheric oxygen atom at its terminal which is bonded to CF.

As specific examples of the compound 3a-1, the following compounds may be mentioned:

$$(FSO_2—CF_2)_2CF—COF,$$

$$(FSO_2—CF_2)_2C(—COF)_2,$$

$$(FSO_2—CF_2)_2CFOCF_2CF_2—COF.$$

In the above production process, each of the compounds 4, 8, 9 and 10 is available as a known compound, and can easily be prepared by a known method.

Further, as the compound 5 in the above production process, the following compound 5a wherein $E^1$ is —COW (wherein W is as defined above) and the following compound 5b wherein $E^1$ is —CH$_2$OH, are easily prepared from products of a decomposition reaction of the compound 2a. In the formulae, $R^{BF}$ is as defined above:

$$R^{BF}—COF \quad (5a)$$

$$R^{BF}—CH_2OH \quad (5b)$$

That is, as the compound 5a is contained together with the compound 3a in the product of the decomposition reaction of the compound 2a, the compound 5a can be recycled. Further, the compound 5b can be obtained by a reduction reaction of the compound 5a. The reduction reaction of the compound 5a may be carried out by e.g. a method of converting the compound 5a into an alkyl ester, and reacting it with a metal hydride in a liquid phase.

The esterification reaction of the compound 5a may be carried out in the same manner as in the esterification reaction as explained for the Process 1-1 for Production of Compound 7. The metal hydride is preferably sodium borohydride, lithium aluminum hydride or the like. The reaction is carried out preferably in the presence of a solvent, and the solvent is preferably tetrahydrofuran, dioxane or the like. Further, in a case that sodium borohydride is employed as the metal hydride, methanol, ethanol or 2-propanol may be used as a solvent. The amount of the solvent to an esterified product of the compound 5a is preferably at least two times by mass, particularly preferably from 5 to 50 times by mass. The reaction temperature is usually preferably from −50° C. to the boiling point of the solvent, particularly preferably from 0° C. to the boiling point of the solvent. The reaction pressure is not particularly limited, and preferably from normal pressure to 2 MPa.

In a case that the compound 5a is directly reduced to obtain the compound 5b, the reduction reaction may be preferably carried out also by a method of bringing the compound 5a into contact with hydrogen gas in the presence of a catalyst. The catalyst in such a method is preferably a paradium, rodium or iridium catalyst. The reaction may be carried out either in the presence or in the absence of a solvent, and it is carried out preferably in the absence of a solvent from the viewpoint of the volume efficiency. The reaction temperature is usually preferably from 0° C. to 200° C. The reaction pressure is not particularly limited, and preferably from normal pressure to 10 MPa.

The process to obtain the compound 5 to be used for Process 2 for Production of Compound 1 from the product in the decomposition reaction of the compound 2a is a process advantageous from environmental and economical viewpoints.

The compound 3 to be obtained by the present invention, which has a —SO$_2$F group at its terminal, is a compound useful as e.g. a starting material of a monomer for an ion-exchange resin. Among the compounds 3, the compound 3a is a compound having both —SO$_2$F groups and —COF group at its molecular terminals, and it can be converted into various useful compounds by a method utilizing reactivity of the —COF group.

For example, the following compound 13a-10 can be produced by pyrolyzing the following compound 3a-2 which is one embodiment of the compound 3a. In the following formulae, $R^{AF1}$ is a (n+1)valent perfluoro saturated hydrocarbon group or a (n+1)valent perfluoro(etheric oxygen atom-containing saturated hydrocarbon) group:

$$(FSO_2—)_n R^{AF1}—CF(CF_3)COF \quad (3a-2)$$

$$(FSO_2—)_n R^{AF1}—CF=CF_2 \quad (13a-10)$$

Further, by adding hexafluoropropylene oxide to the terminal —COF group of the compound 3a obtained by the above process, such a group can be converted into a —CF$_2$OCF(CF$_3$)COF group. Such a group can be converted into a —CF=CF$_2$ group which is a polymerizable unsaturated group, by the same reaction as for the compound 3a-2. Namely, the present invention provides a process for producing the following compound 12a by adding hexafluoropropylene oxide to the compound 3a (in the following formula, m, n and $R^{AF}$ are as defined above):

$$(FSO_2—)_n R^{AF}(—CF_2OCF(CF_3)COF)_m \quad (12a)$$

Addition of hexafluoropropylene oxide may be carried out in accordance with a known method.

The compound 12a is preferably the following compound (12a-1), particularly preferably the following compound (12a-11) (wherein, $R^{CF}$, p, m, a, b and $Q^F$ are as defined above):

$$(FSO_2—)_p R^{CF}(—CF_2OCF(CF_3)COF)_m \quad (12a-1)$$

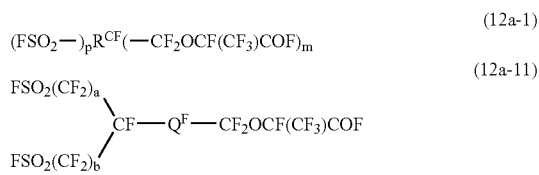
(12a-11)

The —CF(CF$_3$)COF group moiety in the compound 12a can be converted into a —CF=CF$_2$ group by a pyrolytic reaction. Namely, the present invention provides a process for producing the following compound 13b by pyrolyzing the compound 12a. In the following formula, m and n are as defined above. $R^{AF}$ is as defined above, and is preferably a perfluorinated (m+n)valent organic group:

$$(FSO_2—)_n R^{AF}(—CF_2OCF=CF_2)_m \quad (13b)$$

As a process for producing a compound 13b wherein m is 1, a process of reacting the following compound 3a-3 with hexafluoropropylene oxide (HFPO) to form a compound 3a-4, and pyrolyzing it to produce the following compound (13a-20), may be mentioned. In the following formulae, $R^{AF2}$ is a (n+1)valent perfluorinated saturated hydrocarbon group or a (n+1)valent perfluoro(etheric oxygen atom-containing saturated hydrocarbon) group:

$$(FSO_2—)_n R^{AF2}—COF \quad (3a-3)$$

$$(FSO_2—)_n R^{AF2}—CF_2OCF(CF_3)COF \quad (3a-4)$$

$$(FSO_2—)_n R^{AF2}—CF_2OCF=CF_2 \quad (13a-20)$$

A compound having a —CF=CF$_2$ group at the molecular terminal, e.g. compound 13a, 13b or the like, is a compound useful as a monomer for preparation of an ion-exchange membrane.

The compound 13b is preferably the following compound 13b-1 wherein n is 2 or 3 and m is 1 or 2. In the following formula, $R^{CF}$ is a perfluorinated (p+q)valent (i.e. trivalent to pentavalent) organic group having at least two carbon atoms, p is 2 or 3, and q is 1 or 2:

$$(FSO_2—)_p R^{CF}(—CF_2OCF=CF_2)_q \quad (13b-1)$$

The compound 13b-1 is preferably the following compound (13b-11) (in the following formula, a, b, $Q^F$ are as defined above):

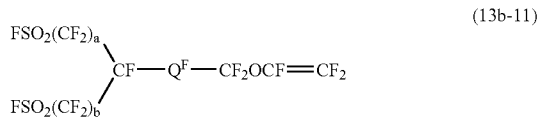
(13b-11)

The pyrolytic reaction of the compound 3a-2 and the compound 12a may be carried out in accordance with a known means (for example, methods as disclosed in Methods of Organic Chemistry (Houben-Weyl), 4th ed., Baasner, B., Hagemann H., Tatlow, J. C., Eds., Georg Thieme, Stuttgart, 1999, Vol, E 10b (Organo-Fluorine Compounds), Pt.1, p. 703., WO02/44138, etc.).

As the pyrolytic reaction, it is preferred to employ a gas phase pyrolytic reaction or a method wherein the —CF(CF$_3$)COF moiety is converted into an alkali metal carboxylate group by reaction with an alkali hydroxide, followed by a pyrolytic reaction in a liquid phase.

The reaction temperature in the gas phase pyrolytic reaction is preferably from 250 to 400° C., particularly preferably from 250 to 350° C. The reaction temperature in the pyrolytic reaction of the alkali carboxylate is preferably from 150 to 350° C., particularly preferably from 200 to 280° C. When the temperature for the pyrolytic reaction is high, such an advantage as a high conversion ratio will be achieved, and when it is low, such an advantage that formation of by-products can be suppressed will be achieved.

As the embodiments of the production process of the present invention, the following examples may be mentioned. In the following formulae, $R^{BF2}$ is a perfluoroalkyl group or a perfluoro(etheric oxygen atom-containing) alkyl group, and is preferably $R^{BF1}$.

PRODUCTION EXAMPLE 1

Example for Production of (FSO$_2$CF$_2$)$_2$CFCOF

The following compound 4-1 and the following compound 5a-1 are subjected to an esterification reaction to form the following compound 6-1, the compound 6-1 is reacted with a thiocyanate to form the following compound 7-1, the compound 7-1 is subjected to an oxidation reaction with chlorine to obtain the following compound 1-1, and then the chlorine atom bonded to SO$_2$ in the compound 1-1 is substituted by fluorine to form the following compound 1F-1. The compound 1F-1 is reacted with fluorine in a liquid phase to form the following compound 2-1, and the compound 2-1 is decomposed to produce the following compound 3-1. Further, the following compound 5a-1 is obtained from the decomposition reaction product, and the obtained compound 5a-1 is used for the reaction with the compound 4-1 in this production process and the same reactions are carried out:

$$(BrCH_2)_2CHCH_2OH \quad (4-1)$$

$$+$$

$$R^{BF2}COF \quad (5a-1)$$

↓

$$(BrCH_2)_2CHCH_2OCOR^{BF2} \quad (6-1)$$

↓

$$(NCSCH_2)_2CHCH_2OCOR^{BF2} \quad (7-1)$$

↓

-continued (ClSO$_2$CH$_2$)$_2$CHCH$_2$OCOR$^{BF2}$   (1-1)

↓

(FSO$_2$CH$_2$)$_2$CHCH$_2$OCOR$^{BF2}$   (1F-1)

↓

(FSO$_2$CF$_2$)$_2$CFCF$_2$OCOR$^{BF2}$   (2-1)

↓

(FSO$_2$CF$_2$)$_2$CFCOF   (3-1)  +  (5a-1)

PRODUCTION EXAMPLE 2

The following compound 4-2 and the compound 5a-1 are subjected to an esterification reaction to form the following compound 6-2, the compound 6-2 is reacted with a thiocyanate to form the following compound 7-2, the compound 7-2 is oxidized by chlorine to obtain the following compound 1-2, and the chlorine atom bonded to SO$_2$ in the compound 1-2 is substituted by fluorine to form the following compound 1F-2. Then, the compound 1F-2 is reacted with fluorine in a liquid phase to form the following compound 2-2, and the compound 2-2 is decomposed to obtain the following compound 3-2 and at the same time to obtain the compound 5a-1. The obtained compound 5a-1 is used for the reaction with the compound 4-2 in this production process and the same reactions are carried out:

(BrCH$_2$)$_2$CHCH$_2$OCH(CH$_3$)CH$_2$OH   (4-2)

+

R$^{BF2}$COF   (5a-1)

↓

(BrCH$_2$)$_2$CHCH$_2$OCH(CH$_3$)CH$_2$OCOR$^{BF2}$   (6-2)

↓

(NCSCH$_2$)$_2$CHCH$_2$OCH(CH$_3$)CH$_2$OCOR$^{BF2}$   (7-2)

↓

(ClSO$_2$CH$_2$)$_2$CHCH$_2$OCH(CH$_3$)CH$_2$OCOR$^{BF2}$   (1-2)

↓

(FSO$_2$CH$_2$)$_2$CHCH$_2$OCH(CH$_3$)CH$_2$OCOR$^{BF2}$   (1F-2)

↓

-continued (FSO$_2$CF$_2$)$_2$CFCF$_2$OCF(CF$_3$)CF$_2$OCOR$^{BF2}$   (2-2)

↓

(FSO$_2$CF$_2$)$_2$CFCF$_2$OCF(CF$_3$)COF   (3-2)  +  (5a-1)

PRODUCTION EXAMPLE 3

The following compound 4-3 and the following compound 5b-1 are subjected to an esterification reaction to form the following compound 6-3, the compound 6-3 is reacted with a thiocyanate to form the following compound 7-3, the compound 7-3 is oxidized by chlorine to form the following compound 1-3, and the chlorine atom bonded to SO$_2$ in the compound 1-3 is substituted by fluorine to form the following compound 1F-3. The compound 1F-3 is reacted with fluorine in a liquid phase to form the following compound 2-3, and the compound 2-3 is decomposed to obtain the following compound 3-1 and at the same time to obtain the compound 5a-1. The obtained compound 5a-1 is reduced to form the compound 5b-1, which is used for the reaction with the compound 4-3 in this production process and the same reactions are carried out:

(BrCH$_2$)$_2$CHCOOH   (4-3)

+

R$^{BF2}$CH$_2$OH   (5b-1)

↓

(BrCH$_2$)$_2$CHCOOCH$_2$R$^{BF2}$   (6-3)

↓

(NCSCH$_2$)$_2$CHCOOCH$_2$R$^{BF2}$   (7-3)

↓

(ClSO$_2$CH$_2$)$_2$CHCOOCH$_2$R$^{BF2}$   (1-3)

↓

(FSO$_2$CH$_2$)$_2$CHCOOCH$_2$R$^{BF2}$   (1F-3)

↓

(FSO$_2$CF$_2$)$_2$CFCOOCF$_2$R$^{BF2}$   (2-3)

↓

(FSO$_2$CF$_2$)$_2$CFCOF   (3-1)  +  (5a-1)

PRODUCTION EXAMPLE 4

The following compound 4-4 and the following compound 5b-1 are subjected to an esterification reaction to form the following compound 6-4, the compound 6-4 is reacted with a thiocyanate to form the following compound 7-4, the compound 7-4 is oxidized by chlorine to obtain the following compound 1-4, and the chlorine atom bonded to $SO_2$ in the compound 1-4 is substituted by fluorine to form the following compound 1F-4. The compound 1F-4 is reacted with fluorine in a liquid phase to form the following compound 2-4, and the compound 2-4 is decomposed to obtain the following compound 3-2 and at the same time to obtain the compound 5a-1. The compound 5a-1 is reduced to form the compound 5b-1, which is used for the reaction with the compound 4-4 in this production process and the same reactions are carried out:

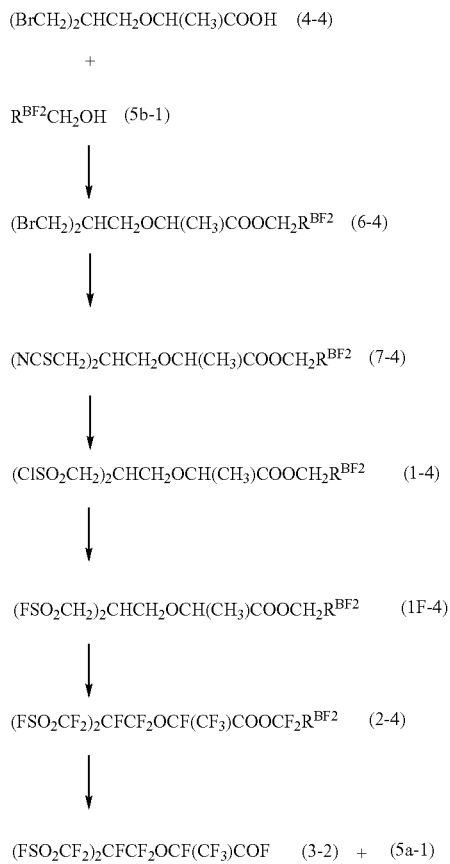

PRODUCTION EXAMPLE 5

The following compound 10-1 and the following compound 5b-1 are subjected to an esterification reaction to form the following compound 11-1, the compound 11-1 is oxidized by chlorine to obtain the following compound 1-5, and the chlorine atom bonded to $SO_2$ in the compound 1-5 is substituted by a fluorine atom to form the following compound 1F-5. The compound 1F-5 is reacted with fluorine in a liquid phase to form the following compound 2-5, and the compound 2-5 is decomposed to obtain the following compound 3-4 and at the same time to obtain the following compound 5a-1. This compound 5a-1 is reduced to form the compound 5b-1, which is used for the reaction with the compound 10-1 in this production process and the same reactions are carried out:

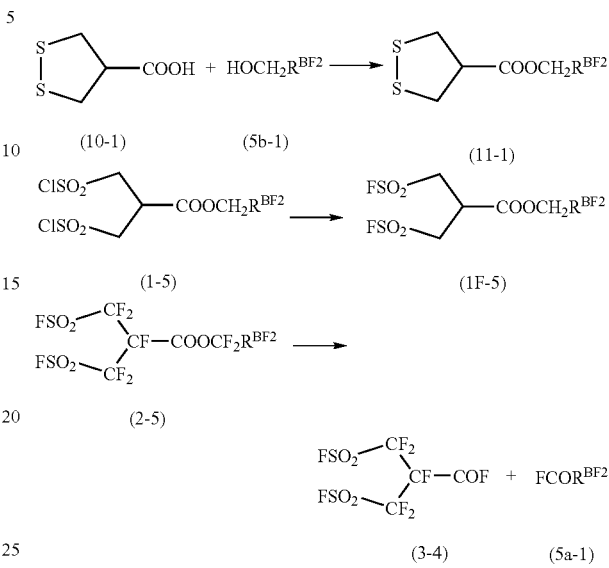

EXAMPLES

Now, the present invention will be described in detail with reference to Examples, but the present invention is not restricted by the Examples. In the following, gas chromatography will be referred to as GC, and GC mass spectrometry will be referred to as GC-MS. The yield means the isolated yield unless otherwise noted. The yield determined from the peak area ratio of the NMR spectrum will be referred to as NMR yield. $CCl_2FCClF_2$ will be referred to as R-113, and tetrahydrofuran as THF. The standard value of the standard substance $CDCl_3$ in the $^{13}C$-NMR was 76.9 ppm. In the quantitative analysis by the $^{19}F$-NMR, $C_6F_6$ was used as the internal standard. The pressure is the gauge pressure unless otherwise noted.

Example 1

Example for Production of $(FSO_2CF_2)_2CFCOF$

Example 1-1

Example for Production of $(BrCH_2)_2CHCH_2OH$ by Reduction Reaction $(BrCH_2)_2CHCOOH$ (70.5 g) and THF (40 mL) were put in a is flask in a nitrogen stream and stirred in an ice bath. A 1M-THF solution (300 mL) of borane was added dropwise thereto over a period of 60 minutes while maintaining the internal temperature to be 10° C. or lower. After completion of the dropwise addition, the temperature was allowed to be room temperature, followed by stirring for 2 hours, and water (20 mL) was added.

Further, a saturated potassium carbonate aqueous solution (50 mL) was added, liquid separation was carried out, extraction with t-butyl methyl ether (80 mL) was carried out four times, and the obtained organic layer was dried over magnesium sulfate, followed by filtration and concentrated to obtain a crude liquid. The crude liquid was distilled to obtain the title compound (49.4 g, boiling point: 83 to 84° C./(0.7×1.33322×10$^5$) Pa, yield: 74%).

$^1$H-NMR (300.4 MHz, CDCl$_3$, TMS) δ: 2.26 (sep, J=5.8 Hz, 1H), 2.31 (s, 1H), 3.55 (dd, J=6.0, 10.5 Hz, 2H), 3.59 (dd, J=5.6, 10.5 Hz, 2H), 3.76 (d, J=6.0 Hz, 2H); IR (neat) 3354.1, 2959.7, 1430.1, 1265.4, 1051.0 cm$^{-1}$.

Example 1-2

Example for Production of (BrCH$_2$)$_2$CHCH$_2$OCOCF(CF$_3$)OCF$_2$CF$_2$CF$_3$ by Esterification Reaction (BrCH$_2$)$_2$CHCH$_2$OH (49.4 g) obtained in Example 1A, methylene chloride (400 mL) and triethylamine (24.0 g) were put in a flask and stirred in an ice bath. FCOCF(CF$_3$)OCF$_2$CF$_2$CF$_3$ (74.3 g) was dropwise added thereto over a period of 60 minutes while maintaining the internal temperature to be 10° C. or lower. After completion of the dropwise addition, the temperature was allowed to be room temperature, followed by stirring for 3 hours, and the content was added to water (400 mL).

The obtained crude liquid was subjected to liquid separation, and the obtained lower layer was washed with a sodium hydrogen carbonate aqueous solution (150 mL) three times and with an ammonium chloride aqueous solution (150 mL) three times, and dried over magnesium sulfate, followed by filtration and concentrated to obtain a crude liquid. The crude liquid was distilled to obtain the title compound (98.4 g, boiling point: 85 to 87° C./(0.7×1.33322×10$^5$) Pa (absolute pressure), yield: 85%).

$^1$H-NMR (300.4 MHz, CDCl$_3$, TMS) δ 2.50 (sep, J=5.8 Hz, 1H), 3.50 (ddd, J=1.8, 5.8, 10.7 Hz, 2H), 3.54 (ddd, J=2.4, 5.8, 10.7 Hz, 2H), 4.49 (dd, J=5.8, 11.3 Hz, 2H), 4.57 (dd, J=6.4, 11.3 Hz, 1H); $^{19}$F-NMR (282.7 MHz; CDCl$_3$, CFCl$_3$) δ −79.8 (1F), −81.1 (3F), −81.9 (3F), −86.2 (1F), −129.1 (2F), −131.2 (1F); IR (neat) 1790.6, 1236.4, 1152.0, 1037.7, 992.6, 747.1 cm$^{-1}$.

Example 1-3

Example for Production of (NCSCH$_2$)$_2$CHCH$_2$OCOCF(CF$_3$)OCF$_2$CF$_2$CF$_3$ Potassium thiocyanate (69.2 g) and dimethylformamide (700 mL) were put in a flask, and (BrCH$_2$)$_2$CHCH$_2$OCOCF(CF$_3$)OCF$_2$CF$_2$CF$_3$ (95.7 g) obtained in Example 1-2 was charged with stirring at room temperature. Stirring was carried out further for 1 hour at 80° C. The content was added to water (1,000 mL), extraction with t-butyl methyl ether (300 mL) was carried out three times, and the obtained organic layer was dried over magnesium sulfate, followed by filtration and concentration to obtain a crude liquid. The crude liquid was purified by silica gel column chromatography (as an eluent, a mixed solvent comprising hexane (10)/ethyl acetate (1) was employed) to obtain the title compound (59.1 g, solid, melting point: 136 to 137° C., yield: 63%).

$^1$H-NMR (300.4 MHz, CDCl$_3$, TMS) δ 2.75 (m, 1H), 3.13 (dd, J=6.8, 14.1 Hz, 2H), 3.22 (dd, J=6.2, 14.1 Hz, 2H), 4.65 (dd, J=4.7, 12.0 Hz, 1H), 4.73 (dd, J=4.7, 12.1 Hz, 1H); $^{19}$F-NMR (282.7 MHz; CDCl$_3$, CFCl$_3$) δ −79.8 (1F), −81.0 (3F), −81.7 (3F), −86.0 (1F), −129.1 (2F), −131.2 (1F) IR (neat) 2157.1, 1768.4, 1232.8, 1151.4, 1036.9, 992.2, 747.6 cm$^{-1}$.

Example 1-4

Example for Production of (ClSO$_2$CH$_2$)$_2$CHCH$_2$OCOCF(CF$_3$)OCF$_2$CF$_2$CF$_3$ by Oxidation Reaction (NCSCH$_2$)$_2$CHCH$_2$OCOCF(CF$_3$)OCF$_2$CF$_2$CF$_3$ (4.8 g) obtained in Example 1-3, water (2 mL) and acetic acid (38 mL) were put in a flask equipped with a dry ice condenser, and chlorine gas was bubbled with stirring at room temperature. The bubbling was stopped when the chlorine gas started being refluxed, and stirring was continued at room temperature for 16 hours. After the system was purged by nitrogen, the content was added to water (80 mL), extraction with t-butyl methyl ether (30 mL) was carried out four times, and the obtained organic layer was dried over magnesium sulfate, followed by filtration and concentration to obtain the title compound (4.4 g, yield: 78%). The product was subjected to the subsequent reaction as it was without purification.

$^1$H-NMR (300.4 MHz, CDCl$_3$, TMS) δ 3.47 (m, 1H), 3.93 (dd, J=6.4, 14.8 Hz, 2H), 4.07 (ddd, J=1.3, 6.0, 14.8 Hz, 2H), 4.74 (dd, J=4.5, 12.0 Hz, 1H), 4.82 (dd, J=4.7, 12.0 Hz, 1H); $^{19}$F-NMR (282.7 MHz; CDCl$_3$, CFCl$_3$) δ −79.7 (1F), −81.0 (3F), −81.7 (3F), −85.9 (1F), −129.0 (2F), −131.2 (1F); IR (neat) 1790.5, 1422.6, 1236.4, 1152.1, 1037.2, 992.5, 809.1, 747.0 cm$^{-1}$.

Example 1-5

Example for Production of (FSO$_2$CH$_2$)$_2$CHCH$_2$OCOCF(CF$_3$)OCF$_2$CF$_2$CF$_3$ by Fluorine Substitution Reaction (ClSO$_2$CH$_2$)$_2$CHCH$_2$OCOCF(CF$_3$)OCF$_2$CF$_2$CF$_3$ (4.0 g) obtained in Example 1-4, potassium hydrogen fluoride (2.4 g), water (30 mL) and acetonitrile (30 mL) were put in a flask, followed by stirring at room temperature for 24 hours. The content was added to water (50 mL), extraction with t-butyl methyl ether (30 mL) was carried out three times, and the obtained organic layer was dried over magnesium sulfate, followed by filtration and concentration to obtain a crude liquid. The crude liquid was purified by silica gel column chromatography (as an eluent, a mixed solvent comprising hexane (10)/ethyl acetate (1) was employed) to obtain the title compound (1.5 g, yield: 53%).

$^1$H-NMR (300.4 MHz, CDCl$_3$, TMS) δ 3.24 (sep, J=5.8 Hz, 1H), 3.66 (ddd, J=3.4, 6.4, 15.4 Hz, 2H), 3.77 (ddd, J=1.1, 4.7, 15.4 Hz, 2H), 4.66 (dd, J=4.7, 12.0 Hz, 1H), 4.82 (dd, J=4.7, 12.0 Hz, 1H); $^{19}$F-NMR (282.7 MHz; CDCl$_3$, CFCl$_3$) δ 59.1 (2F), −79.7 (1F), −81.0 (3F), −81.7 (3F), −86.1 (1F), −129.1 (2F), −131.3 (1F); IR (neat) 1791.8, 1429.1, 1237.5, 1037.2, 993.6 cm$^{-1}$.

Example 1-6

Example for Production of (FSO$_2$CF$_2$)$_2$CFCF$_2$OCOCF(CF$_3$)OCF$_2$CF$_2$CF$_3$ by Liquid Phase Fluorination Into a 500 mL autoclave made of nickel, R-113 (312 g) was added, stirred and maintained at 25° C. At the gas outlet of the autoclave, a cooler maintained at 20° C., a packed layer of NaF pellets and a cooler maintained at −10° C. were installed in series. Further, a liquid-returning line was installed to return a condensed liquid from the cooler maintained at −10° C. to the autoclave.

Nitrogen gas was blown to the autoclave at room temperature for 1 hour, and then fluorine gas diluted to 20% with nitrogen gas (hereinafter referred to as 20% diluted fluorine gas) was blown at room temperature at a flow rate of 9.19 L/h for 0.5 hour. While blowing the 20% diluted fluorine gas at the same flow rate, the internal pressure of the autoclave was elevated to 0.20 MPa, and the 20% diluted fluorine gas was blown further for 0.5 hour.

Then, while blowing the 20% diluted fluorine gas at the same flow rate, a solution having the compound (3 g) obtained in Example 1-5 dissolved in R-113 (30 g) was injected over a period of 1.0 hour.

Then, while maintaining the internal pressure of the reactor to be 0.20 MPa, 9 mL of a R-113 solution having a benzene concentration of 0.01 g/mL was injected while raising the temperature from 25° C. to 40° C., and the benzene solution inlet of the autoclave was closed, and stirring was continued for 0.3 hour.

Then, while maintaining the internal pressure of the reactor to be 0.20 MPa and the internal temperature of the reactor to be 40° C., 6 mL of the above benzene solution was injected, the benzene solution inlet of the autoclave was closed, and stirring was continued for 0.3 hour. Further, the same operation was repeated three times. The total amount of benzene injected was 0.34 g, and the total amount of R-113 injected was 33 mL.

Further, while blowing the 20% diluted fluorine gas at the same flow rate, stirring was continued for 1 hour. Then, the internal pressure of the reactor was allowed to be normal pressure, and nitrogen gas was blown for 1 hour. The product was analyzed by $^{19}$F-NMR and as a result, it was confirmed to contain the title compound with a yield of 30%.

$^{19}$F-NMR (282.7 MHz; CDCl$_3$, CFCl$_3$) δ 45.9 (2F), −71.6 to −80.8 (3F), −81.9 (6F), −86.5 (1F), −92.8 to −105.0 (4F), −130.0 (2F), −132.2 (1F), −178.6 (1F).

Example 1-7

Example for Production of $(FSO_2CF_2)_2CFCOF$ by Decomposition Reaction $(FSO_2CF_2)_2CFCF_2OCOCF(CF_3)OCF_2CF_2CF_3$ (3.6 g) obtained in Example 1-6 was charged into a flask together with NaF powder (0.02 g) and heated at 140° C. for 10 hours in an oil bath with vigorous stirring. At the upper portion of the flask, a reflux condenser having the temperature maintained at 20° C. was installed. After cooling, a liquid sample (3.4 g) was recovered. As a result of the analysis by GC-MS, $CF_3CF_2CF_2OCF(CF_3)COF$ (NMR yield: 72.0%) and $(FSO_2CF_2)_2CFCOF$ (NMR yield: 70.9%) were confirmed to be the main products.

Example 1-8

Recycle of $CF_3CF_2CF_2OCF(CF_3)COF$ $CF_3CF_2CF_2OCF(CF_3)COF$ obtained in Example 1-7 is reacted with $(BrCH_2)_2CHCH_2OH$ under the same conditions as the above esterification reaction to obtain $(BrCH_2)_2CHCH_2OCOCF(CF_3)OCF_2CF_2CF_3$. Employing the obtained $(BrCH_2)_2CHCH_2OCOCF(CF_3)OCF_2CF_2CF_3$, the same reactions as in Example 1-3 to 1-7 are carried out to obtain $(FSO_2CF_2)_2CFCOF$ and $CF_3CF_2CF_2OCF(CF_3)COF$.

Example 2

Example for Production of $(FSO_2CF_2)_2CFOCF_2CF_2COF$

Example 2-1

Example for Production of $(C_6H_5CH_2SCH_2)_2CHOH$

In a nitrogen stream, a solution having sodium hydroxide (4.0 g) dissolved in ethanol (80 mL) was put in a flask and stirred in an ice bath. Benzyl mercaptan (12.5 g) was added dropwise thereto over a period of 10 minutes while keeping the internal temperature to be 15° C. or lower. Further, epichlorohydrine (4.7 g) was dropwise added thereto over a period of 10 minutes while keeping the internal temperature to be 20° C. or lower. After completion of the dropwise addition, the temperature was allowed to be room temperature, followed by stirring for 4 hours, and water (200 mL) was added.

Extraction with t-butyl methyl ether (50 mL) was carried out four times, and the obtained organic layer was washed with an aqueous ammonium chloride solution and dried over magnesium sulfate, followed by filtration and concentration to obtain a crude liquid. The crude liquid was purified by silica gel column chromatography (as an eluent, a mixed solvent comprising hexane (5)/ethyl acetate (1) was employed) to obtain the title compound (15.8 g, yield: at least 98%).

$^1$H-NMR (300.4 MHz, CDCl$_3$, TMS) δ 2.47 (dd, J=7.5, 13.9 Hz, 2H), 2.58 (dd, J=4.7, 13.9 Hz, 2H), 2.75 (d, J=3.2 Hz, 1H), 3.63 to 3.73 (m, 1H), 3.68 (s, 4H), 7.18 to 7.33 (m, 10H); IR (neat) 3445.8, 3060.2, 3026.9, 2913.4, 1493.6, 1452.8, 1239.7, 1071.2, 1028.2, 767.6, 700.5 cm$^{-1}$.

Example 2-2

Example for Production of $(C_6H_5CH_2SCH_2)_2CHOCH_2CH=CH_2$

Anhydrous THF (150 mL) was put in a flask in a nitrogen stream, and 60% sodium hydride (4.2 g) was added thereto, followed by stirring in an ice bath. $(C_6H_5CH_2SCH_2)_2CHOH$ (29.2 g) was added dropwise thereto over a period of 15 minutes while maintaining the internal temperature to be 5° C. or lower. Stirring was carried out for 30 minutes, and allyl bromide (12.0 g) was added dropwise thereto over a period of 10 minutes while maintaining the internal temperature to be 5° C. or lower. After completion of the dropwise addition, the temperature was allowed to be room temperature, followed by stirring for 20 hours, and water (400 mL) was added.

Extraction with t-butyl methyl ether (70 mL) was carried out four times, and the obtained organic layer was washed with an aqueous ammonium chloride solution and dried over magnesium sulfate, followed by filtration and concentration to obtain a crude liquid. The crude liquid was purified by silica gel column chromatography (as an eluent, a mixed solvent comprising hexane (5)/ethyl acetate (1) was employed) to obtain the title compound (32.3 g, yield: 98%).

$^1$H-NMR (300.4 MHz, CDCl$_3$, TMS) δ 2.59 (dd, J=5.8, 13.7 Hz, 2H), 2.64 (dd, J=5.8, 13.7 Hz, 2H), 3.47 (qui, J=5.8 Hz, 1H), 3.70 (s, 4H), 3.95 (dm, J=5.8 Hz, 2H), 5.14 (dm, J=10.3 Hz, 1H), 5.23 (dm, J=17.1 Hz, 1H), 5.87 (ddt, J=10.3, 17.1, 5.8 Hz, 1H), 7.18 to 7.34 (m, 10H); $^{13}$C-NMR (75.45 MHz, CDCl$_3$, CDCl$_3$) δ 34.4, 37.0, 70.8, 78.4, 117.0, 126.9, 128.4, 128.9, 134.8, 138.3; IR (neat) 3061.0, 3027.3, 2918.3, 1493.7, 1452.9, 1071.6, 923.1, 767.4, 700.5 cm$^{-1}$.

Example 2-3

Example for Production of $(C_6H_5CH_2SCH_2)_2$CHOCH$_2$CH$_2$CH$_2$OH

In a nitrogen stream, a 1M-THF solution (88 mL) of borane was put in a flask, and cyclohexene (14.5 g) was added thereto, followed by stirring in an ice bath. Stirring was carried out for 3 hours in such a state. $(C_6H_5CH_2SCH_2)_2$CHOCH$_2$CH=CH$_2$ (25.4 g) was added dropwise thereto over a period of 10 minutes while maintaining the internal temperature to be 5° C. or lower. After completion of the dropwise addition, stirring was carried out at a temperature of 10° C. or lower for 19 hours. A 3M sodium hydroxide aqueous solution (30 mL) was added dropwise thereto over a period of 15 minutes while maintaining the internal temperature to be 10° C. or lower. Stirring was continued for 15 minutes, and 30% hydrogen peroxide solution (30 mL) was added dropwise thereto over a period of 30 minutes while maintaining the internal temperature to be 20° C. or lower.

An aqueous solution having potassium carbonate (150 g) dissolved in water (150 mL) was added thereto, and an organic layer was separated by liquid separation. The obtained aqueous layer was extracted with t-butyl methyl ether (50 mL) three times, and the resulting organic layers were collected and washed with an ammonium chloride aqueous solution and dried over magnesium sulfate, followed by filtration and concentration to obtain a crude liquid. The crude liquid was purified by silica gel column chromatography (as an eluent, a mixed solvent comprising hexane (2)/ethyl acetate (1) was employed) to obtain $(C_6H_5CH_2SCH_2)_2$CHOCH$_2$CH$_2$CH$_2$OH (20.4 g, yield: 76%).

$^1$H-NMR (300.4 MHz, CDCl$_3$, TMS) δ 1.75 (qui, J=5.7 Hz, 2H), 2.46 (t, J=5.7 Hz, 1H), 2.56 (dd, J=6.2, 13.7 Hz, 2H), 2.62 (dd, J=5.8, 13.7 Hz, 2H), 3.34 (qui, J=5.8 Hz, 1H), 3.55 (t, J=5.8 Hz, 2H), 3.69 (s, 4H), 3.74 (q, J=5.4 H, 2H), 7.20 to 7.35 (m, 10H); $^{13}$C-NMR (75.45 MHz, CDCl$_3$, CDCl$_3$) δ 32.1, 34.6, 36.8, 61.0, 68.3, 78.6, 127.0, 128.4, 128.5, 128.9, 138.1; IR (neat) 3439.8, 3026.9, 2917.3, 2870.8, 1493.7, 1452.9, 1239.7, 1088.5, 1072.0, 768.9, 701.2 cm$^{-1}$.

Example 2-4

Example for Production of $(C_6H_5CH_2SCH_2)_2$CHOCH$_2$CH$_2$CH$_2$OCOCF(CF$_3$)OCF$_2$CF$_2$CF$_3$ by Esterification Reaction $(C_6H_5CH_2SCH_2)_2$CHOCH$_2$CH$_2$CH$_2$OH (25.2 g), methylene chloride (200 mL) and triethylamine (10.1 g) were put in a flask and stirred in an ice bath. FCOCF(CF$_3$)OCF$_2$CF$_2$CF$_3$ (31.5 g) was added dropwise thereto over a period of 40 minutes while maintaining the internal temperature to be 5° C. or lower. After completion of the dropwise addition, the temperature was allowed to be room temperature, followed by stirring for 3 hours, and the content was added to water (200 mL).

The obtained crude liquid was subjected to liquid separation, and the obtained lower layer was washed twice with an aqueous sodium hydrogen carbonate solution (80 mL) and with an aqueous ammonium chloride solution (80 mL) twice and dried over magnesium sulfate, followed by filtration and concentration to obtain a crude liquid.

The crude liquid was purified by silica gel column chromatography (eluent: mixed solvent comprising hexane (10) and ethyl acetate (1) to obtain $(C_6H_5CH_2SCH_2)_2$CHOCH$_2$CH$_2$CH$_2$OCOCF(CF$_3$)OCF$_2$CF$_2$CF$_3$ (49.2 g, yield: at least 98%).

$^1$H-NMR (300.4 MHz, CDCl$_3$, TMS) δ 1.92 (qui, J=6.0 Hz, 2H), 2.55 (dd, J=6.0, 13.5 Hz, 2H), 2.61 (dd, J=5.6, 13.5 Hz, 2H), 3.32 (qui, J=5.8 Hz, 1H), 3.44 (t, J=5.8 Hz, 2H), 3.68 (s, 4H), 4.48 (dt, J=2.8, 6.4 Hz, 2H), 7.20 to 7.34 (m, 10H); $^{19}$F-NMR (282.7 MHz; CDCl$_3$, CFCl$_3$) δ −79.7 (1F), −81.1 (3F), −81.9 (3F), −86.2 (1F), −129.2 (2F), −131.1 (1F); IR (neat) 3029.5, 2917.3, 1782.5, 1494.6, 1454.1, 1335.1, 1285.3, 1235.9, 1200.6, 1151.9, 1112.7, 1037.4, 992.1, 747.2, 701.1 cm$^{-1}$.

Example 2-5

Example for Production of $(ClSO_2CH_2)_2$CHOCH$_2$CH$_2$CH$_2$OCOCF(CF$_3$)OCF$_2$CF$_2$CF$_3$ by Oxidation Reaction $(C_6H_5CH_2SCH_2)_2$CHOCH$_2$CH$_2$CH$_2$OCOCF(CF$_3$)OCF$_2$CF$_2$CF$_3$ (42.4 g), water (30 mL) and acetic acid (270 mL) were put in a flask, and chlorine gas was bubbled with stirring at room temperature. The bubbling was stopped when chlorine started being refluxed, and stirring was carried out at room temperature for 16 hours in such a state. After the system was purged by nitrogen, the content was added to water (600 mL), extraction with t-butyl methyl ether (100 mL) was carried out four times, and the organic layer was dried over magnesium sulfate, followed by filtration and concentration to obtain the title compound as a crude product.

The product was subjected to the subsequent reaction as it was without purification.

$^1$H-NMR (300.4 MHz, CDCl$_3$, TMS) δ 2.06 (qui, J=6.0 Hz, 2H), 3.79 (t, J=5.8 Hz, 2H), 4.04 to 4.16 (m, 4H), 4.50 (dt, J=3.0, 6.0 Hz, 2H), 4.64 (qui, J=5.6 Hz, 1H); $^{19}$F-NMR (282.7 MHz; CDCl$_3$, CFCl$_3$) δ −79.7 (1F), −81.1 (3F), −81.9 (3F), −86.2 (1F), −129.1 (2F), −131.2 (1F); IR (neat) 3002.5, 2953.1, 1780.8, 1419.9, 1338.8, 1287.8, 1234.6, 1199.5, 1153.0, 1108.3, 1038.0, 991.9, 802.8, 747.1 cm$^{-1}$.

Example 2-6

Example for Production of $(FSO_2CH_2)_2$CHOCH$_2$CH$_2$CH$_2$OCOCF(CF$_3$)OCF$_2$CF$_2$CF$_3$ by Fluorine Substitution Reaction $(ClSO_2CH_2)_2$CHOCH$_2$CH$_2$CH$_2$OCOCF(CF$_3$)OCF$_2$CF$_2$CF$_3$ (51.3 g) obtained in Example 2-5, potassium hydrogen fluoride (20.3 g), water (250 mL) and acetonitrile (250 mL) were put in a flask and stirred at room temperature for 24 hours.

The content was added to water (500 mL), extraction with t-butyl methyl ether (100 mL) was carried out three times, and the obtained organic layer was dried over magnesium sulfate, followed by filtration and concentration to obtain a crude liquid. The crude liquid was purified by silica gel column chromatography (as an eluent, a mixed solvent comprising hexane (5)/ethyl acetate (1) was employed) to obtain the title compound (19.3 g). The yield from $(C_6H_5CH_2SCH_2)_2$CHOCH$_2$CH$_2$CH$_2$OCOCF(CF$_3$)OCF$_2$CF$_2$CF$_3$ was 53%.

$^1$H-NMR (300.4 MHz, CDCl$_3$, TMS) δ 2.06 (qui, J=6.0 Hz, 2H), 3.73 to 3.82 (m, 6H), 4.42 to 4.57 (m, 3H); $^{19}$F-NMR (282.7 MHz; CDCl$_3$, CFCl$_3$) δ 61.6 (2F), −80.3 (1F), −81.7 (3F), −82.6 (3F), −87.0 (1F), −130.2 (2F), −132.2 (1F); IR (neat) 3003.8, 2953.4, 1781.1, 1420.5, 1339.4, 1288.6, 1236.3, 1200.5, 1154.1, 1109.1, 1038.7, 992.5, 804.5, 747.4 cm$^{-1}$.

Example 2-7

Example for Production of (FSO$_2$CF$_2$)$_2$ CFOCF$_2$CF$_2$CF$_2$OCOCF(CF$_3$)OCF$_2$CF$_2$CF$_3$ by Liquid Phase Fluorination Reaction The same reaction as in Example 1-6 was carried out except that the operation of injecting the solution having the compound (3 g) obtained in Example 1-5 dissolved in R-113 (30 g) over a period of 1.0 hour was changed to an operation of injecting a solution having the product (3 g) obtained in Example 2-6 dissolved in R-113 (90 g) over a period of 2.8 hours. In Example 2-7, the total amount of benzene injected was 0.22 g, and the total amount of R-113 injected was 21 mL. The product was analyzed by $^{19}$F-NMR and as a result, it was confirmed to contain the title compound with a yield of 50%.

$^{19}$F-NMR (282.7 MHz; CDCl$_3$, CFCl$_3$) δ 46.6 (2F), −79.3 to −80.0 (1F), −82.0 (8F), −87.1 (3F), −104.5 (4F), −128.4 to −129.3 (2F), −130.2 (2F), −132.3 (1F), −133.8 (1F)

Example 2-8

Example for Production of (FSO$_2$CF$_2$)$_2$ CFOCF$_2$CF$_2$COF by Decomposition Reaction (FSO$_2$CF$_2$)$_2$CFOCF$_2$CF$_2$CF$_2$OCOCF(CF$_3$)OCF$_2$CF$_2$CF$_3$ (2.9 g) obtained in Example 2-7 was charged into a flask together with NaF powder (0.02 g) and heated at 140° C. for 10 hours in an oil bath with vigorous stirring. At the upper portion of the flask, a reflux condenser having the temperature maintained at 20° C. was installed. After cooling, a liquid sample (2.6 g) was recovered. As a result of analysis by GC-MS, CF$_3$CF$_2$CF$_2$OCF(CF$_3$)COF (NMR yield: 68.0%) and (FSO$_2$CF$_2$)$_2$CFOCF$_2$CF$_2$COF (NMR yield: 72.4%) were confirmed as the main products.

Example 3

Example for Production of (FSO$_2$CF$_2$)$_2$ CFOCF$_2$CF$_2$CF$_2$OCF(CF$_3$)COF (FSO$_2$CF$_2$)$_2$CFOCF$_2$CF$_2$COF (82.7 g) obtained in the same method as in Example 2 was charged into a 200 mL autoclave together with CsF powder (2.33 g) and diglyme (33.0 g), and hexafluoropropylene oxide (33.0 g) was introduced with stirring under cooling with ice. Stirring was carried out for 1 hour in such a state, and the content was distilled under reduced pressure to obtain a fraction (38.9 g, boiling point: 79° C. to 80° C./667 Pa). The fraction was analyzed by NMR and GC and as a result, formation of the title compound (GC purity: 86%, conversion ratio: 57%, NMR yield: 60%) was confirmed. Further, (FSO$_2$CF$_2$)$_2$ CFOCF$_2$CF$_2$COF (35.9 g) was recovered.

$^{19}$F-NMR (282.7 MHz; CDCl$_3$, CFCl$_3$) δ 46.7 (2F), 26.7 (1F), −79.0 (1F), −79.3 (2F), −82.1 (3F), −86.4 (1F), −104.5 (4F), −128.2 (2F), −130.9 (1F), −133.7 (1F).

Example 4

Example for Production of (FSO$_2$CF$_2$)$_2$ CFOCF$_2$CF$_2$CF$_2$OCF=CF$_2$

Potassium hydrogen carbonate (6.03 g) was charged into a flask together with monoglyme (59 mL), and (FSO$_2$CF$_2$)$_2$ CFOCF$_2$CF$_2$CF$_2$OCF(CF$_3$)COF (35.6 g) obtained in Example 3 was added dropwise thereto with stirring under cooling with ice. Vacuum drying was carried out for 30 minutes and then vacuum drying was further carried out at 120° C. for 48 hours to obtain (FSO$_2$CF$_2$)$_2$ CFOCF$_2$CF$_2$CF$_2$OCF(CF$_3$)COOK (21.1 g). The obtained (FSO$_2$CF$_2$)$_2$CFOCF$_2$CF$_2$CF$_2$OCF(CF$_3$)COOK was heated at 200° C. under 400 Pa (absolute pressure), and generated gas was collected in a trap cooled with liquid nitrogen to obtain a liquid (8.35 g). The liquid was analyzed by NMR and GC and as a result, formation of the title compound (NMR yield: 25%, GC purity: 87%) was confirmed. Further, as another component, formation of (FSO$_2$CF$_2$)$_2$ CFOCF$_2$CF$_2$CF$_2$OCFHCF$_3$ was confirmed.

$^{19}$F-NMR (282.7 MHz; CDCl$_3$, CFCl$_3$) δ 46.7 (2F), −79.4 (2F), −85.6 (2F), −103.1 to −105.4 (4F), −113.3 (1F), −121.7 (1F), −128.3 (2F), −133.7 (1F), −135.7 (1F).

INDUSTRIAL APPLICABILITY

According to the production process of the present invention, sulfonyl fluoride compounds having various structures can be produced from easily available materials effectively at a low cost. Further, in the process of the present invention, a reaction product can be recycled. Accordingly, it is an economical production process in which the amount of the material used and the amount of waste can be reduced.

The entire disclosure of Japanese Patent Application No. 2003-270412 filed on Jul. 2, 2003 including specification, claims, and summary is incorporated herein by reference in its entirety.

What is claimed is:

1. A process for producing a compound represented by the following formula (3a-1), which comprises oxidizing a compound represented by the formula (7-a) by reacting it with chlorine in a solvent comprising water to obtain a compound represented by the following formula (1-a), fluorinating the compound represented by the formula (1-a) to obtain a compound represented by the following formula (1F-a), reacting the compound represented by the formula (1F-a) with fluorine in a liquid phase to obtain a compound represented by the following formula (2-a), and carrying out a decomposition reaction of an ester bond in the compound represented by the formula (2-a):

  (7-a)

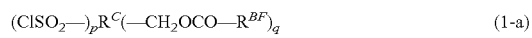  (1-a)

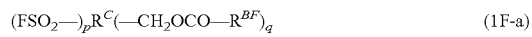  (1F-a)

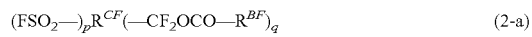  (2-a)

  (3a-1)

wherein Y is a hydrogen atom, a monovalent organic group or a —SO$_3^-$M$^+$ group (wherein M is an alkali metal atom), R$^C$ is a (p+q)valent organic group having at least two carbon atoms and containing no fluorine atom, R$^{CF}$ is a group having R$^C$ perfluorinated and represents a perfluorinated (p+q)valent organic group having at least two carbon atoms, $R^{BF}$ is a perfluorinated monovalent organic group, p is 2 or 3, and q is 1 or 2.

2. A compound represented by the following formula (3a-1):

$$(FSO_2\text{---})_p R^{CF}(\text{---}COF))_q \qquad (3a\text{-}1)$$

wherein $R^{CF}$ is a perfluorinated (p+q)valent organic group having at least two carbon atoms, p is 2 or 3, and q is 1 or 2.

3. A compound represented by the following formula (3a-11):

wherein a is an integer of from 1 to 3, b is an integer of from 1 to 3, and $Q^F$ is a single bond or a $C_{1-4}$ perfluoroalkylene group which may contain an etheric oxygen atom.

4. A process for producing a compound represented by the following formula (12a), which comprises adding hexafluoropropylene oxide to a compound represented by the following formula (3a):

$$(FSO_2\text{---})_n R^{AF}(\text{---}COF)_m \qquad (3a)$$

$$(FSO_2\text{---})_n R^{AF}(\text{---}CF_2OCF(CF_3)COF)_m \qquad (12a)$$

wherein $R^{AF}$ is the same group as $R^A$ or a (n+m)valent organic group having $R^A$ fluorinated, n is an integer of 2 or more, and m is an integer of 1 or more.

5. A compound represented by the following formula (12a-1):

$$(FSO_2)_p R^{CF}(\text{---}CF_2OCF(CF_3)COF))_q \qquad (12a\text{-}1)$$

wherein $R^{CF}$ is a perfluorinated (p+q)valent organic group having at least two carbon atoms, p is 2or 3, and q is 1 or 2.

6. A compound represented by the following formula (12a-11):

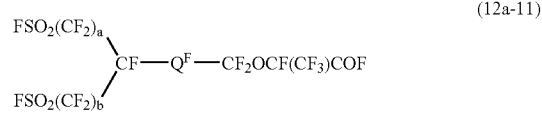

wherein a is an integer of from 1 to 3, b is an integer of from 1 to 3, $Q^F$ is a single bond or a $C_{1-6}$ perfluoroalkylene group which may contain an etheric oxygen atom.

7. The process according to claim 1, wherein said solvent further comprises acetic acid.

8. The process according to claim 1, wherein said solvent further comprises acetonitrile.

9. The compound according to claim 2, wherein $R^{CF}$ is a perfluorinated (p+q)valent organic group having at least three carbon atoms.

10. The compound according to claim 2, wherein $R^{CF}$ is a perfluorinated (p+q)valent organic group having from three to sixteen carbon atoms.

11. The compound according to claim 2, wherein $R^{CF}$ is a perfluorinated (p+q)valent organic group having from four to sixteen carbon atoms.

12. The compound according to claim 2, wherein $R^{CF}$ is a perfluorinated (p+q)valent organic group having from five to sixteen carbon atoms.

13. The compound according to claim 3, wherein said compound is represented by the following formula:

$$(FSO_2\text{---}CF_2)_2CF\text{---}COF$$

wherein a is 1, b is 1, and $Q^F$ is a single bond.

14. The compound according to claim 3, wherein $Q^F$ is a $C_{1-6}$ perfluoroalkylene group having a terminal etheric oxygen bonded to CF, which is a perfluorinated trivalent organic group.

15. The compound according to claim 13, wherein said compound is represented by the following formula:

$$(FSO_2\text{---}CF_2)_2CFOCF_2CF_2COF$$

wherein a is 1, b is 1, and $Q^F$ is a $C_2$ perfluoro(oxyethylene) group.

* * * * *